United States Patent
Boileau et al.

(10) Patent No.: US 10,765,524 B2
(45) Date of Patent: Sep. 8, 2020

(54) PROSTHESIS FOR A FRACTURED LONG BONE

(71) Applicant: Tornier, Montbonnot-Saint-Martin (FR)

(72) Inventors: Pascal Boileau, Nice (FR); Jean-Emmanuel Cardon, Domene (FR); Bertrand Claizergues, Montbonnot (FR); Vincent Coulange, Lyons (FR); Benjamin Dassonville, Saint Hilaire du Touvet (FR); Vincent Gaborit, Saint martin d'Heres (FR)

(73) Assignee: Tornier, Montbonnot-Saint-Martin (FR)

( * ) Notice: Subject to any disclaimer, the term of this patent is extended or adjusted under 35 U.S.C. 154(b) by 46 days.

(21) Appl. No.: 16/259,501

(22) Filed: Jan. 28, 2019

(65) Prior Publication Data
US 2019/0231544 A1 Aug. 1, 2019

(30) Foreign Application Priority Data

Jan. 31, 2018 (EP) .................................... 18305101

(51) Int. Cl.
*A61F 2/32* (2006.01)
*A61F 2/28* (2006.01)
(Continued)

(52) U.S. Cl.
CPC .............. *A61F 2/4059* (2013.01); *A61F 2/28* (2013.01); *A61F 2/30734* (2013.01); *A61F 2/4014* (2013.01); *A61B 17/86* (2013.01); *A61F 2/4003* (2013.01); *A61F 2002/2835* (2013.01); *A61F 2002/2853* (2013.01); *A61F 2002/30092* (2013.01); *A61F 2002/30332* (2013.01); *A61F 2002/30433* (2013.01);
(Continued)

(58) Field of Classification Search
CPC ............. A61F 2/4059; A61F 2/28; A61F 2/32
See application file for complete search history.

(56) References Cited

U.S. PATENT DOCUMENTS 6,398,812 B1 6/2002 Masini
8,623,092 B2 1/2014 Bickley et al.
(Continued)

FOREIGN PATENT DOCUMENTS

FR 3 025 089 3/2016
GB 1 504 055 3/1978
WO WO 2006/126238 11/2006

OTHER PUBLICATIONS

European Search Report issued in EP Application No. 18305101, dated Jul. 10, 2018, in 2 pages.

*Primary Examiner* — Jason-Dennis N Stewart
(74) *Attorney, Agent, or Firm* — Knobbe, Martens Olson & Bear, LLP

(57) ABSTRACT

The invention concerns a prosthesis comprising: a stem part comprising: a rod, configured for being inserted into a medullary cavity of a diaphyseal fragment of a fractured long bone, for securing the stem part to the diaphyseal fragment, and an epiphyseal end, fixedly secured to the rod by means of at least one linker leg of the stem part, so that a gap is formed between the epiphyseal end and the rod along said at least one linker leg; and an implant distinct from the stem part and comprising: an internal part located at least partially within the gap, and at least one fastener for fastening epiphyseal fragments of the fractured long bone to the stem part, said at least one fastener being secured to the internal part.

18 Claims, 15 Drawing Sheets

(51) Int. Cl.
  *A61F 2/40*    (2006.01)
  *A61F 2/30*    (2006.01)
  *A61B 17/86*    (2006.01)
  *A61F 2/46*    (2006.01)

(52) U.S. Cl.
  CPC ............ *A61F 2002/30593* (2013.01); *A61F 2002/30827* (2013.01); *A61F 2002/30879* (2013.01); *A61F 2002/4062* (2013.01); *A61F 2002/4066* (2013.01); *A61F 2002/4631* (2013.01); *A61F 2210/0014* (2013.01); *A61F 2310/00023* (2013.01)

(56) References Cited

U.S. PATENT DOCUMENTS

| | | |
|---|---|---|
| 2004/0230311 A1 | 11/2004 | Cyprien et al. |
| 2007/0244565 A1 | 10/2007 | Stchur |
| 2010/0268232 A1 | 10/2010 | Betz et al. |
| 2010/0288421 A1 | 11/2010 | Kujawski et al. |
| 2014/0121709 A1 | 5/2014 | Gonzalez-Hernandez |
| 2015/0190237 A1 | 7/2015 | Bonin, Jr. et al. |
| 2015/0238324 A1 | 8/2015 | Nebosky et al. |
| 2017/0043052 A1 | 2/2017 | San Antonio et al. |

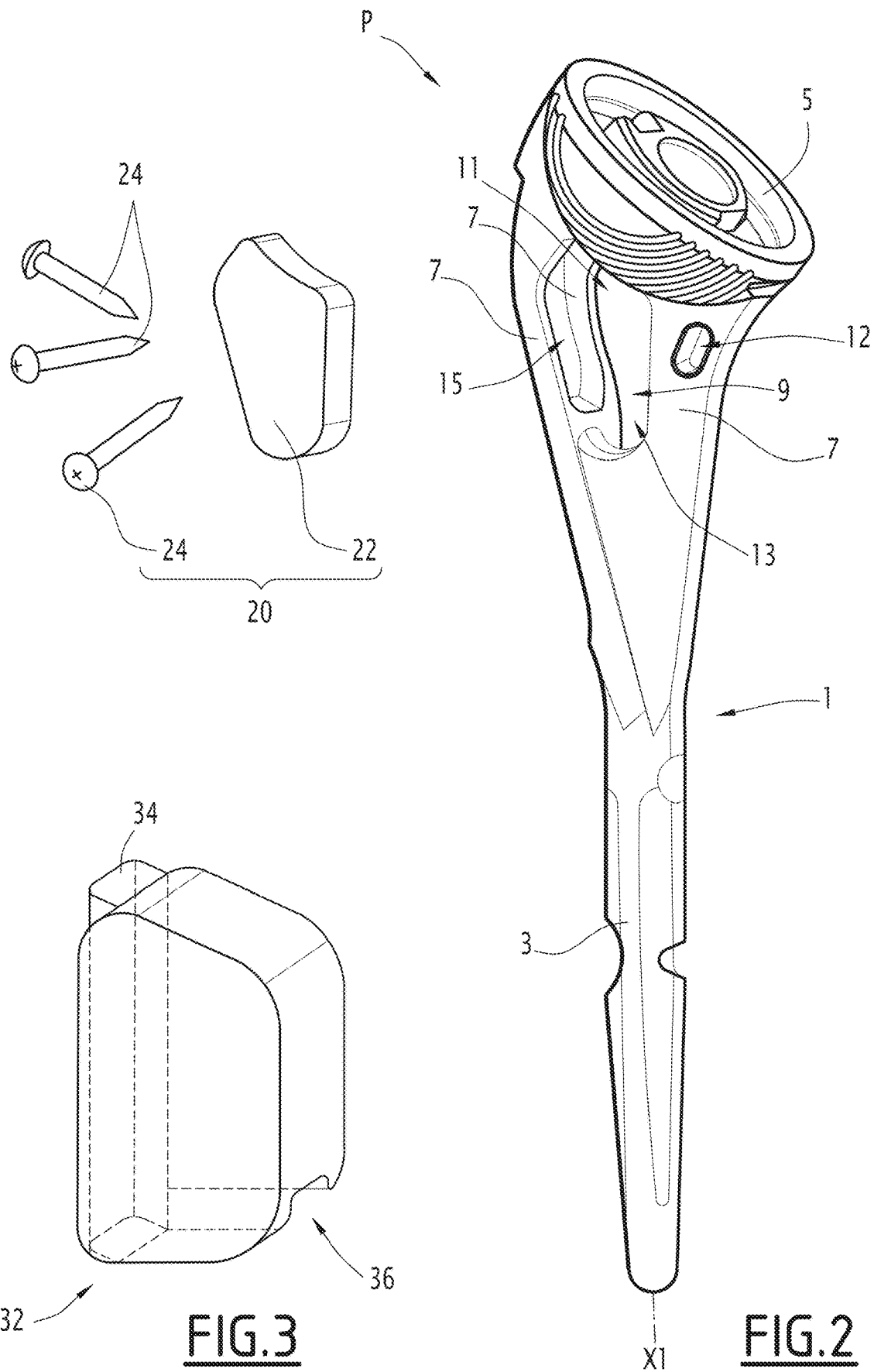

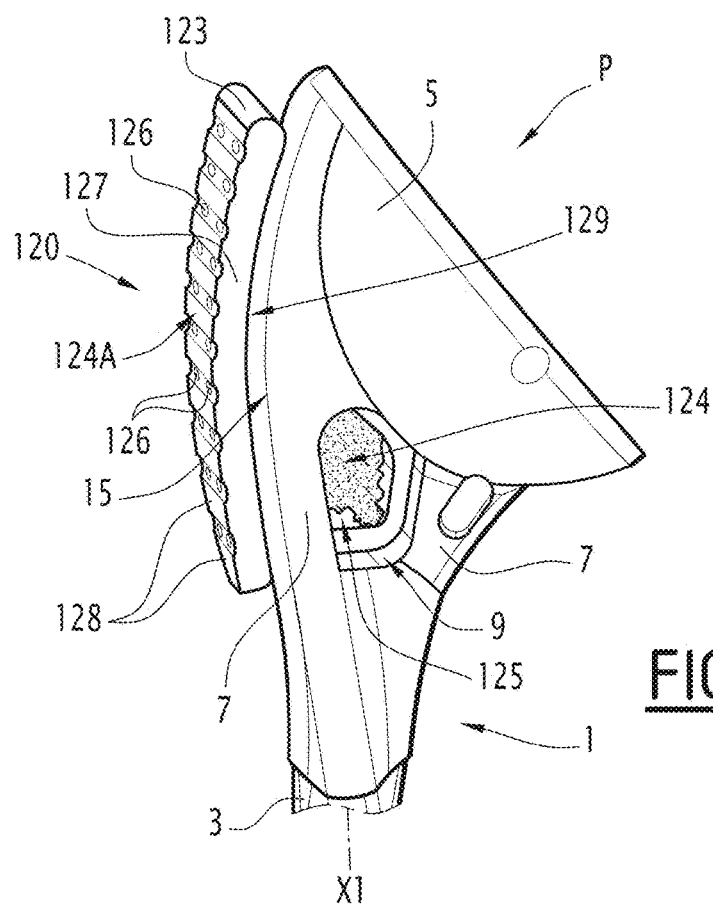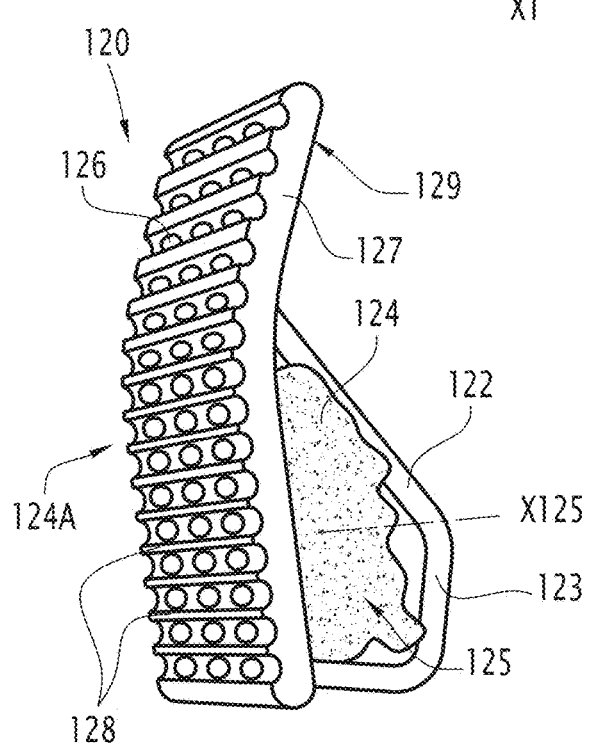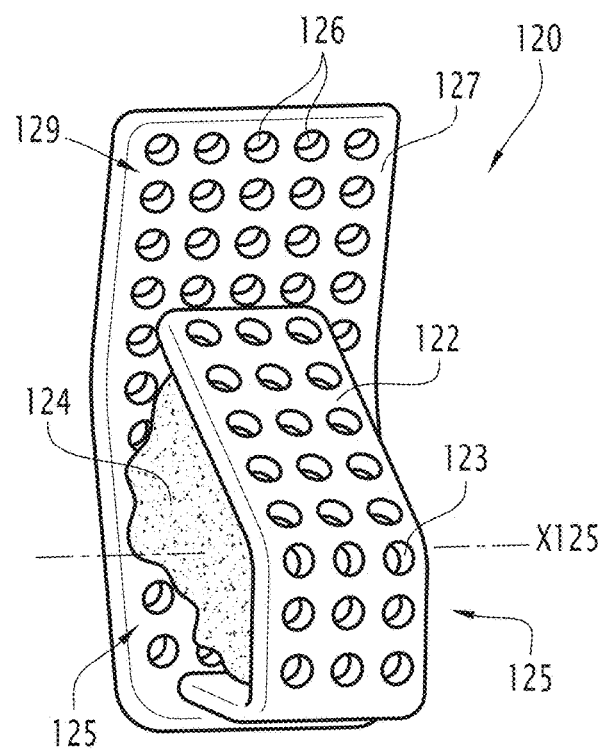

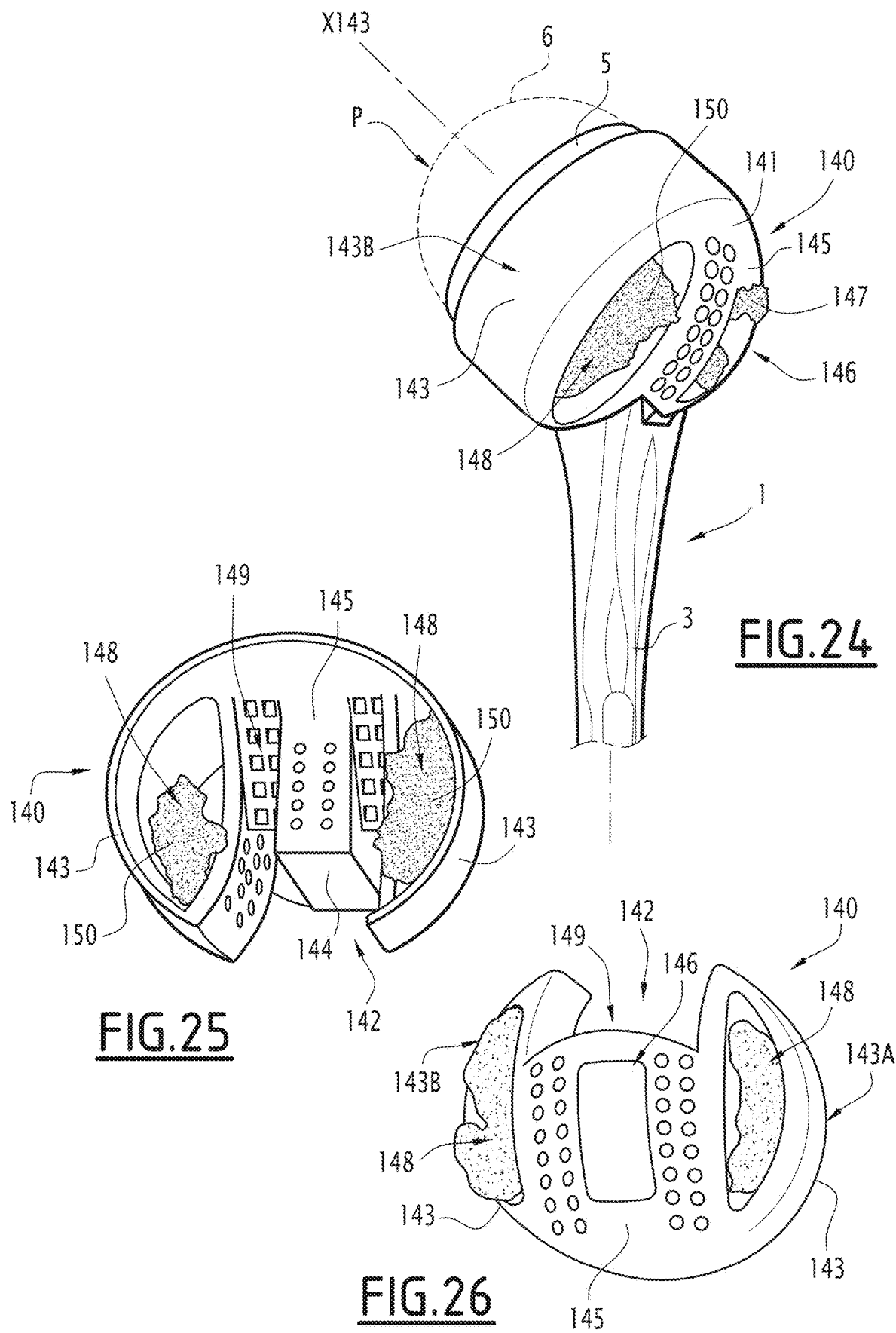

PROSTHESIS FOR A FRACTURED LONG BONE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The invention relates to a prosthesis for a fractured long bone.

The invention relates to the domain of joint arthroplasty, preferably shoulder arthroplasty, alternatively to hip arthroplasty. The invention preferably applies to human patients, but could also be applied to animal patients.

Description of the Related Art

US2004/0230311 A1 discloses a shoulder prosthesis to be used to replace the upper humerus in certain fracture types. This known prosthesis comprises a stem to be inserted in the canal of the humerus, an intermediary part reduced to a medial pillar and a head which is a hollow and generally spherical cap. The head of the prosthesis is coated with an osteoconductive material, the lateral aspect of the medial pillar as well as the upper part of the stem being also coated with the same material. An epiphyso-metaphyseal space is delineated by these components, in which a solid autogenous bone graft is fitted. Union can be achieved between the coated parts of the prosthesis, the bone graft and the tuberosities reattached to the humerus shaft, secured to holes of the medial pillar and between themselves. This known type of prosthesis implies suturing the tuberosities to holes of the medial pillar for reattaching the tuberosities thereto.

However, the sutures sometimes do not prevent tuberosities to migrate after surgery because of the movements of the patient, all the more as muscles are usually anchored to said tuberosities. Also, attaching the tuberosities by suturing requires a high dexterity for the surgeon.

SUMMARY OF THE INVENTION

The aim of the invention is to overcome the defects of the prior art discussed above.

In particular, it is an aim of the present invention to provide a new prosthesis for a fractured long bone making the surgery easier and preventing post-surgery migration of the tuberosities, thus optimizing the healing process of the patient pursuant to surgery.

The invention is defined below:

A prosthesis for a fractured long bone, the prosthesis comprising:
  a stem part comprising:
    a rod, configured for being inserted into a medullary cavity of a diaphyseal fragment of the fractured long bone, for securing the stem part to the diaphyseal fragment, and
    an epiphyseal end, fixedly secured to the rod by means of at least one linker leg of the stem part, so that a gap is formed between the epiphyseal end and the rod along said at least one linker leg; and
  an implant distinct from the stem part and comprising:
    an internal part located at least partially within the gap, and
    at least one fastener for fastening epiphyseal fragments of the fractured long bone to the stem part, said at least one fastener being secured to the internal part.

The invention allows securing the epiphyseal fragments to the prosthesis, by means of said at least one fastener, in addition or alternatively to suture. Thus, a more convenient, stable and durable securing of the epiphyseal fragments is achieved. Since the internal part of the implant is a distinct part relative to the stem part, to be positioned within the gap, the surgeon may choose in situ, depending on the situation, whether this internal part should be provided to the prosthesis or not: the stem part may be used without the implant.

Further optional and advantageous features of the invention are defined below:
  said at least one fastener comprises a screw, positioned into the internal part.
  the internal part has an elastic tongue allowing snap-fitting of the internal part into the gap, for securing the internal part to the gap.
  the internal part comprises at least one expansible body, having a retracted configuration allowing insertion of the expansible body into the gap, and an expanded configuration preventing extraction of the expansible body from the gap, thereby securing the expansible body to the gap, the expansible body being put in the expanded configuration by securing the fastener thereto.
  the implant comprises at least one exterior part, at least a partially located at the periphery of the stem part, along said at least one linker leg, said exterior part being secured to the internal part.
  the stem part defines a main axis passing through the rod, the gap and the epiphyseal end; and said at least one exterior part comprises an axial through-opening, the stem part being inserted through the through-opening along the main axis so as to be at least partially wrapped by the exterior part for securing the exterior part to the stem part.
  the internal part comprises a synthetic plastic material.
  the synthetic plastic material of the internal part comprises Polyethylene or Poly-Ether-Ether-Ketone.
  the internal part comprises a mesh metallic material or a porous metallic material.
  the metallic material of the internal part comprises Titanium and/or Nitinol.
  at least a part of the implant, comprises a peripheral shell and at least one bone graft core received within the peripheral shell.
  said at least a part of the implant, which comprises the peripheral shell and said at least one bone graft core, is the internal part.
  the peripheral shell comprises a biomaterial.
  the peripheral shell comprises a degradable polymer or degradable metal.
  the peripheral shell comprises at least one of the following composites of materials: a composite of hydroxyapatite and tricalciumphosphate, a composite of polylactide-co-glycolide and tricalciumphosphate, a composite of poly-L-lactide and tricalciumphosphate.
  the implant comprises barbs protruding outwardly from the implant, outside of the gap.
  at least a part of the implant is obtained by additive manufacturing.

the prosthesis is a shoulder prosthesis for a fractured humerus.

In US2004/0230311 A1, although the bone graft may contribute to good healing of the tuberosities, the bone graft needs to be shaped for fitting in the epiphyso-metaphyseal space. When the bone graft is obtained from another bone part of the patient, such as the humeral head, the surgeon has to shape this graft in situ, which is time consuming and requires much dexterity. Also, due to the mechanical properties of the bone graft, it may be difficult to obtain an appropriate shape even if specific tools are used.

The aim of the invention is to overcome the defects of the prior art discussed above.

In particular, it is an aim of the present invention to provide a new prosthesis for a fractured long bone promoting bone ingrowth and easier to implement.

The invention relates to a prosthesis for a fractured long bone, the prosthesis comprising:
a stem part comprising:
  a rod, configured for being inserted into a medullary cavity of a diaphyseal fragment of the fractured long bone, for securing the stem part to the diaphyseal fragment, and
  an epiphyseal end, fixedly secured to the rod by means of at least one linker leg of the stem part, so that a gap is formed between the epiphyseal end and the rod along said at least one linker leg; and
an implant distinct from the stem part and being positioned adjacent to said at least one linker leg, the implant comprising a peripheral shell and at least one bone graft core received within the peripheral shell.

This invention allows one or more bone graft cores to be positioned within a prefabricated peripheral shell of more precise shape than the bone graft. Thanks to the peripheral shell, the implant may be better secured to the stem part, for example by fitting the implant within the gap, the shape of the shell corresponding to the shape of the gap. The peripheral shell is preferably made of biomaterial, so that bone ingrowth is promoted as efficiently as in the prior art where only the bone graft is provided. Thus, the advantages of a precise shape are combined with bone ingrowth capability. The shape of the peripheral shell may also be chosen for improving the securing of the epiphyseal fragments to the prosthesis. For example, the shape may be chosen so as to correspond to the shape of the epiphyseal fragments and/or for gripping said fragments. Since the implant is a distinct part relative to the stem part, the surgeon may chose in situ, depending on the situation, whether this implant should be included into the prosthesis or not. Thus, the stem part may be used without the implant.

Further optional and advantageous features of the invention are defined as follows:
  the peripheral shell comprises a biomaterial;
  the peripheral shell comprises at least one of the following composites: a composite of hydroxyapatite and tricalciumphosphate, a composite of polylactide-co-glycolide and tricalciumphosphate, a composite of poly-L-lactide and tricalciumphosphate;
  the peripheral shell comprises a degradable polymer or degradable metal;
  the peripheral shell comprises a synthetic plastic material, preferably comprising Polyethylene or Poly-Ether-Ether-Ketone;
  the peripheral shell comprises a mesh metallic material or a porous metallic material, preferably comprising Titanium or Nitinol;
  the peripheral shell is obtained by additive manufacturing;
  the implant comprises barbs positioned protruding outwardly from the implant;
  the peripheral shell and said at least one bone graft core form an internal part of the implant, located at least partially within the gap;
  the implant comprises at least one fastener for fastening epiphyseal fragments of the fractured long bone to the stem part, said at least one fastener being secured to the internal part;
  said at least one fastener comprises a screw, positioned into the internal part;
  the internal part has an elastic tongue allowing snap-fitting of the internal part into the gap, for securing the internal part to the gap;
  the peripheral shell and said at least one bone graft core form at least one exterior part of the implant, at least partially located at the periphery of the stem part, along said at least one linker leg, said exterior part being secured to the stem part through the gap;
  at least two exterior parts are provided, said exterior parts being secured to each other, so that the exterior parts are mechanically secured to the stem part;
  a primary exterior part of the exterior parts comprises a primary fastener and a secondary exterior part of the exterior parts comprises a secondary fastener complementary with the primary fastener, the primary fastener being configured to cooperate with the secondary fastener for fixing the primary exterior part to the secondary exterior part;
  the stem part defines a main axis passing through the rod, the gap and the epiphyseal end and said at least one exterior part comprises an axial through-opening, the stem part being inserted through the through-opening along the main axis so as to be at least partially wrapped by the exterior part for securing the exterior part to the stem part;
  the implant comprises:
    an internal part comprising a peripheral shell and at least one bone graft core and
    at least one exterior part comprising a peripheral shell and at least one bone graft core, the exterior part being secured to the internal part.

In the case of a prosthesis similar to the one disclosed in US2004/0230311 A1, it may be difficult for the surgeon to secure epiphyseal fragments of certain shapes, or fragments that are very fragile or thin, to said prosthesis.

The aim of the invention is to overcome the defects of the prior art discussed above.

In particular, it is an aim of the present invention to provide a new prosthesis for a fractured long bone facilitating securing of epiphyseal fragments thereto, or replacing of non-viable epiphyseal fragments.

The invention relates to a prosthesis for a fractured long bone, the prosthesis comprising:
a stem part comprising:
  a rod, configured for being inserted into a medullary cavity of a diaphyseal fragment of the fractured long bone, for securing the stem part to the diaphyseal fragment, and
  an epiphyseal end, fixedly secured to the rod by means of at least one linker leg of the stem part, so that a gap is formed between the epiphyseal end and the rod along said at least one linker leg; and
an implant distinct from the stem part and comprising at least one exterior part, at least a partially located at the periphery of the stem part, along said at least one linker leg, said exterior part being secured to the stem part through the gap.

In this invention, the implant is distinct from the stem part, so that the surgeon may choose in situ whether the stem part should be provided with the exterior part or not depending on the situation. Thus, the stem part may be used without the implant. Attaching the exterior part to the stem part through the gap allows an easy and reliable securing of the exterior part thereto. One or more epiphyseal fragment(s) may be secured to the exterior part. The exterior part may structurally reinforce the fragment secured thereto. The fragment may be backed by the exterior part to which said fragment is attached. Thus, even thin or fragile fragments may be reattached to the stem part. Otherwise, one or more of the exterior parts may replace one of the fragments, not reintroduced into the patient. The presence of the exterior part(s) allows, for a single stem part, to obtain patient-specific or at least desired peripheral shape of the prosthesis, so that the surgeon may modify and adapt the prosthesis to any situation, by providing the appropriate exterior part.

Further optional and advantageous features of the invention are defined below:
- at least two exterior parts are provided, said exterior parts being secured to each other, so that the exterior parts are mechanically secured to the stem part;
- a primary exterior part of the exterior parts comprises a primary fastener and a secondary exterior part of the exterior parts comprises a secondary fastener complementary with the primary fastener, the primary fastener being configured to cooperate with the secondary fastener for fixing the primary exterior part to the secondary exterior part;
- the implant further comprises an internal part located at least partially within the gap, and to which said at least one exterior part is secured;
- the stem part defines a main axis passing through the rod, the gap and the epiphyseal end;
- said at least one exterior part comprises an axial through-opening, the stem part being inserted through the through-opening along the main axis so as to be at least partially wrapped by the exterior part for securing the exterior part to the stem part;
- the implant comprises at least one fastener for fastening epiphyseal fragments of the fractured long bone to the stem part;
- said at least one fastener is secured to said at least one exterior part;
- said at least one fastener is secured to the internal part;
- the internal part has an elastic tongue allowing snap-fitting of the internal part into the gap, for securing the internal part to the gap;
- said at least one fastener, by means of which said at least one exterior part is secured to the internal part, comprises a screw, positioned into the internal part;
- the internal part comprises at least one expansible body, having a retracted configuration allowing insertion of the expansible body into the gap, and an expanded configuration preventing extraction of the expansible body from the gap, thereby securing the expansible body to the gap, the expansible body being put in the expanded configuration by securing the fastener thereto;
- the implant, in particular said at least one exterior part, comprises a synthetic plastic material, preferably comprising Polyethylene or Poly-Ether-Ether-Ketone;
- the implant, in particular said at least one exterior part, comprises a mesh metallic material or a porous metallic material, preferably comprising Titanium and/or Nitinol;
- the implant, in particular said at least one exterior part, comprises a biomaterial;
- the implant, in particular said at least one exterior part, comprises at least one of the following composites: a composite of hydroxyapatite and tricalciumphosphate, a composite of polylactide-co-glycolide and tricalciumphosphate, a composite of poly-L-lactide and tricalciumphosphate;
- the implant, in particular said at least on exterior part, comprises a degradable polymer or degradable metal;
- said at least one exterior part comprises a peripheral shell and at least one bone graft core received within the peripheral shell,
- the internal part comprises a peripheral shell and at least one bone graft core received within the peripheral shell;
- the implant comprises barbs positioned along the exterior part.

BRIEF DESCRIPTION OF THE DRAWINGS

Further advantages and advantageous features of the invention are disclosed in the following description, provided in reference to the appended drawings, solely for exemplary non-limitative purpose.

In the drawings:

FIG. 2 is an exploded view of the prosthesis of FIG. 1;

FIG. 3 is a schematic perspective view of an implant for a prosthesis according to another embodiment of the invention;

FIG. 17 is a schematic perspective view of a prosthesis according to another embodiment of the invention;

FIGS. 18 and 19 are schematic perspective views of an implant of the prosthesis of FIG. 17, under two different orientations;

FIG. 24 is a schematic perspective view of a prosthesis according to another embodiment of the invention;

FIGS. 25 and 26 are a schematic perspective views of an implant of the prosthesis of FIG. 24, under two different orientations;

DETAILED DESCRIPTION OF THE PREFERRED EMBODIMENT

The prosthesis P of FIGS. 1-18 are prosthesis P for a fractured long bone, in particular a fractured humerus. Thus the prosthesis P of FIGS. 1-18 are designed for shoulder arthroplasty.

Figure 1:
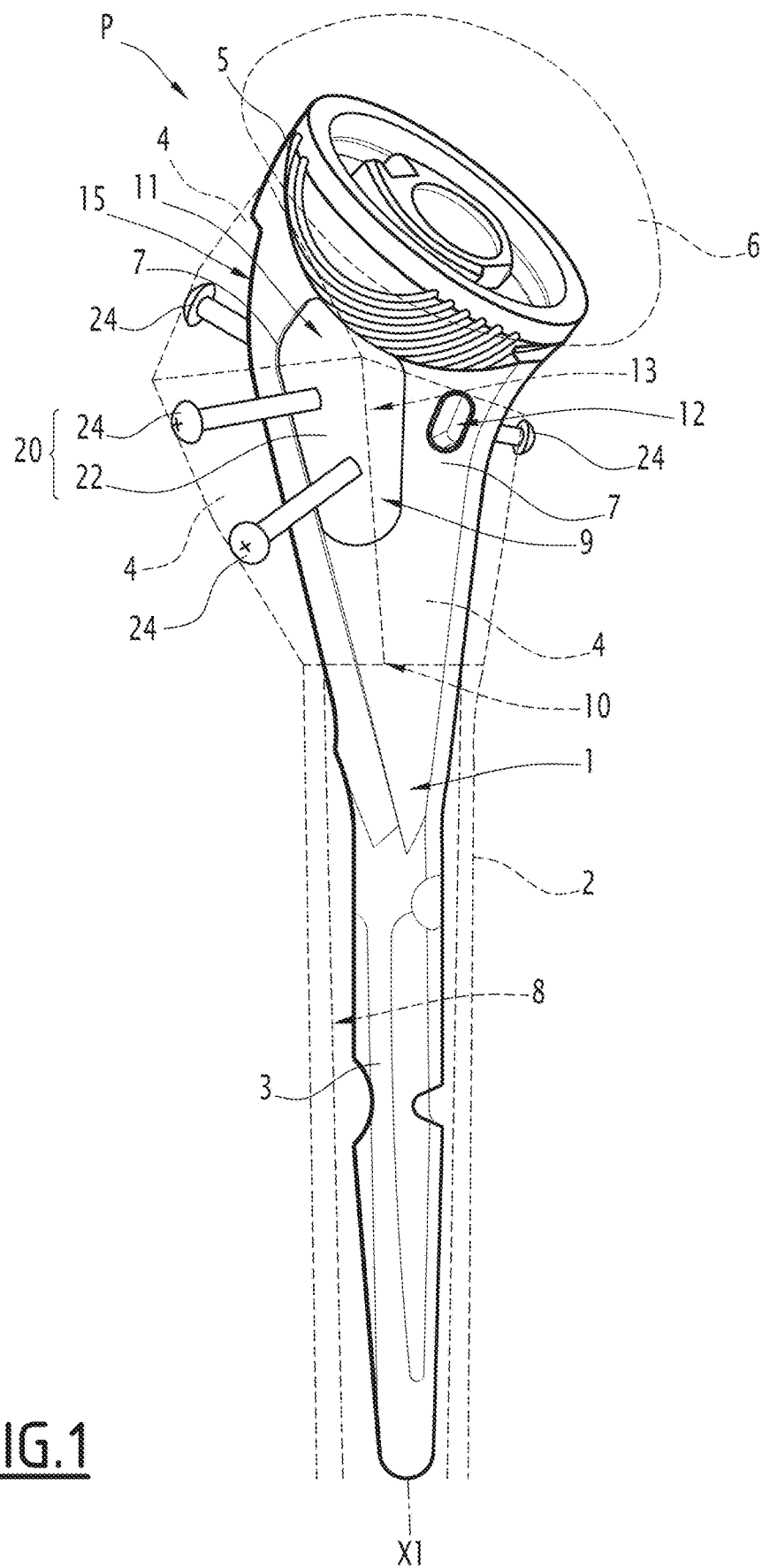
FIG. 1 is a schematic perspective view of a prosthesis according to an embodiment of the invention.

As illustrated schematically in dashed lines on FIG. 1, the fractured long bone comprises:
- a diaphyseal fragment 2, of generally tubular shape, comprising a medullary cavity 8, the cavity 8 being opened at a proximal end 10 of the fragment 2, where the bone is fractured, and
- three epiphyseal fragments 4, or tuberosities, to be positioned at the end 10 of the fragment 2 for reconstructing the original bone.

Depending on the fracture type, more or less than three fragments 4 may be formed from the initial tuberosities of the patient's bone. Muscles of the patient may originally be anchored to all or some of the fragments 4.

The initial long bone may have comprised a head for forming a joint with another bone, in this case a humeral head for forming the shoulder joint with the glenoid of a scapula of the patient. However, in the present case, the initial humeral head is replaced by a prosthetic head 6 shown schematically in dashed lines on FIG. 1. The illustrated prosthetic head 6 is a spherical head, although an inverted head or concave head may be used instead. In other embodiments, all or part of the initial head may be kept instead.

The embodiments disclosed herein may also apply to other fractured long bones and joints than fractured humerus and shoulder, such as fractured femur and hip.

All prostheses P of FIGS. 1-18 comprise the same stem part 1.

The stem part 1 of each embodiment comprises a rod 3, configured for being inserted into the medullary cavity 8 of the fragment 2, for securing the stem part 1 to the fragment 2. Preferably, the rod 3 is fitted into the cavity 8, for example conically fitted. Bone ingrowth promoting materials, cement, fasteners or a combination of known techniques may be operated for securing the rod 3 to the fragment 2. The end of the rod 3 is directed towards a distal end of the fragment 2, and inserted through the proximal end 10 thereof.

The stem part 1 of each prosthesis P according to the invention comprises an epiphyseal end 5. The epiphyseal end 5 is located opposite to the rod 3, along a main axis X1 of the stem part 1, axis X1 being coaxial with the rod 3. The end 5 emerges from the fragment 2. The end 5 may bear the abovementioned head 6, either prosthetic or made of the patient's original head fragment. The head 6 is positioned at a proximal side of the end 5.

The stem part 1 of each embodiment comprises three linker legs 7 approximately parallel to axis X1, or slightly inclined (angle) relative to said axis X1. Each leg 7 is advantageously of reduced section compared to the rod 3 and compared to the end 5. Each leg 7 links a distal side of the end 5 to a proximal end of the rod 3. The legs 7 are preferably distributed around axis X1. Thus, the proximal end of the rod 3 faces the distal side of the end 5, along axis X1.

As depicted on FIGS. 1-18, one of the linker legs 7 may have a through-hole 12, for example for securing suture or other components.

The end 5 is fixedly secured to the rod 3 by means of the linker legs 7 of the stem part 1. Thus, a gap 9 is formed between the epiphyseal end 5 and the rod 3 along the linker legs 7. The axis X1 passes through the gap 9. In other words, the gap 9 is delineated by:
- the rod 3, in particular the proximal end thereof,
- the epiphyseal end 5, in particular the distal side thereof, and
- the linker legs 7.

More or less than three legs 7 may be provided for the stem part 1. At the minimum, only one leg 7 is provided.

The epiphyseal fragments 4 are secured to the stem part around axis X1, approximately at the level of the gap 9 height along axis X1. In other words, the fragments 4 are reattached along the legs 7.

When two or more legs 7 are provided for the stem part 1, at least one through-opening is delineated by two of said legs 7, the rod 3 and the end 5, so that the gap 9 may be accessed from outside of the stem part 1 through said through-opening. In the example of stem part 1 depicted on FIGS. 1-18, where three legs 7 are provided, three through openings 11, 13 and 15 are delineated, the opening 11 being visible on FIG. 1, and the three openings 11, 13 and 15 being visible on FIG. 2. In case where the prosthesis P is a shoulder prosthesis, the openings 11 and 13 are anteroposterior, while the opening 15 is lateral. More generally, these through openings are radial relative to axis X1.

Preferably, the stem part 1 is made of a material with mechanical properties adapted to withstand at least as much mechanical stress than the original bone and to have the same structural function than the original bone. For example, the rod 3, the end 5 and the legs 7 may comprise a bio-compatible metallic material, synthetic plastic material, ceramic material, or any other suitable material, or a combination of such materials. Preferably, the chosen materials are durable once implanted in the body, in other words, not bioresorbable.

If the prosthesis P is a shoulder prosthesis, it may further comprise a glenoid part, configured to form a prosthetic joint together with the stem part. In this case, the glenoid part is connected to the epiphyseal end of the stem part, in an articulated way.

Each prosthesis P of FIGS. 1-18 further comprises a respective implant, each implant being a separate structure from the stem part 1. In other words, the stem part and the implant are distinct and may be separated from each other. In each embodiment, the implant is positioned adjacent to the linker legs 7.

Focusing on FIGS. 1 and 2, the prosthesis P comprises an implant 20. The implant 20 comprises an internal part 22, preferably entirely positioned within the gap 9, between the legs 7 and between the rod 3 and the end 5.

In preferred embodiments, the internal part 22 has a general shape of a parallelepiped, a brick, or a prism with a trapezoid base.

In some embodiments, the internal part 22 may partially extend out of the gap 9, for example through one or more of the openings 11, 13 and 15. In this case however, the internal part 22 is preferably mostly enclosed within the gap 9.

The internal part 22 may be made of one integral part, in other words a single piece, which is the case on FIGS. 1 and 2. Further embodiments disclosed below show cases where the internal part is made of several parts combined.

The internal part 22 of FIGS. 1 and 2 preferably comprises a material softer than the material of the stem part 1.

The internal part 22 may comprise a material configured to be durable once implanted in the body.

Alternatively, the material of the internal part 22 is degradable, or bioresorbable, so that the internal part 22 is partially or totally resorbed after a certain amount of time when implanted in the patient's body. This can be obtained with a degradable polymer, a degradable metal, or a degradable biomaterial.

The internal part 22 may comprise a synthetic plastic material. "Synthetic plastic material" means that the material is constituted of macromolecules obtained by polymerization, polycondensation or polyaddition or the like. Preferably, the internal part 22 is entirely comprised of such a synthetic plastic material. Preferably, the synthetic plastic material may include, but is not limited to polyethylene (PE), or a copolymer thereof. Alternatively or additionally, the plastic material may include Poly-Ether-Ether-Ketone (PEEK) or a copolymer thereof.

For cases where the material is intended to be bioresorbable or degradable once implanted within the patient's body, degradable polymers may be used. Preferably, the internal part 22 comprises one or both of the following degradable polymers: polylactide-co-glycolide and poly-L-lactide. Additionally or alternatively, the degradable materials may include polyanhydrides, polyurethanes, and polysaccharides.

Alternatively or additionally, the internal part 22 comprises a biologic material or a bio-ceramic, herein designated as "biomaterial". Preferably, the internal part 22 is entirely made of such a biomaterial. This biomaterial may comprise one or both of the following materials: hydroxyapatite and tricalciumphosphate. A biomaterial comprising both hydroxyapatite and tricalciumphosphate is preferred.

Alternatively, the internal part 22 comprises a composite, comprising a biomaterial and a degradable polymer. Preferably, the internal part 22 comprises at least one of the following composites:
  a composite of polylactide-co-glycolide and tricalciumphosphate and
  a composite of poly-L-lactide and tricalciumphosphate.

Alternatively or additionally, the internal part 22 comprises a metallic material. Preferably, the internal part 22 is entirely comprised of such a metallic material.

The metallic material may be chosen to be durable once implanted in the patient's body. For example, the metallic material may comprise titanium. Alternatively or additionally, the metallic material may comprise nitinol. The metallic material may be an alloy of one or more of the abovementioned metallic materials.

Alternatively, a bioresorbable metal may be chosen. Preferably, the internal part 22 has a porous structure. Such a structure may promote bone ingrowth for improving healing. In particular if a metallic material is chosen, such a porous structure may also ensure the softness of the internal part 22.

If chosen porous, the internal part 22 preferably comprises a biomaterial and/or a degradable polymer as defined above. Alternatively, a metallic mesh or lattice structure may be chosen.

Alternatively, the internal part 22 may be provided with a solid structure, in other words, a full structure, without pores.

The internal part 22 may comprise a material, being a composite of the abovementioned materials. The internal part 22 may be entirely made of this composite.

The internal part 22 may be made specifically to a patient, namely be patient-specific. The internal part 22 may be obtained by additive manufacturing, especially if a metallic material is chosen.

Preferably, the internal part 22 is shaped corresponding to the shape of the gap 9, so that the internal part 22 may be fitted into the gap 9. Preferably, the internal part 22 is mounted into the gap 9 through the opening 15. Preferably, the internal part 22 is mounted with force-fitting.

At least a part of the implant 20 may be implemented to the stem part 1 for adapting the prosthesis P to different applications. This part is preferably the internal part 22. For example, a left shoulder and a right shoulder prosthesis may be obtained with a stem part of the same reference, by combining said stem part with an implant 20 specific to a right shoulder or an implant 20 specific to a left shoulder. Thus, fewer references of stem parts are necessary.

The implant 20 of FIGS. 1 and 2 comprises screws 24, implanted or positioned into the internal part 22. Preferably, each screw 24 is screwed to the internal part 22. The internal part 22 may optionally comprise pre-drilled holes for positioning the screws 24 therein.

Each screw 24 protrudes from the internal part 22 through one of the openings 11, 13 or 15 of the stem part 1. Each screw 24 is oriented approximately radially to axis X1. For the case of a shoulder prosthesis, the screws 24 may be oriented along anterior, posterior or lateral directions.

The screws 24 are positioned so as to secure the epiphyseal fragments 4 to the stem part 1. Each fragment 4 is preferably locked between a head of the concerned screw 24 and the stem part 1. Each screw 24 passes through a hole provided through one of the fragments 4. One or more screws 24 may be implemented for securing respectively each of the fragments 4.

Thus, the fragments 4 may be secured to the stem 1 by means of the screws 24, so that securing is made easier and more reliable than in the prior art. Thus, the risk of postoperative migration of the fragments 4 is highly reduced. Depending on the material of the internal part 22, bone ingrowth and healing may still be promoted.

Each screw may have a differential-pitch. In other words, a distal part of the screw may have a screw-thread of a first value, whereas a proximal part of the screw may have a screw-thread of a second value different from the first value. The differential pitch may provide compression or pre-stressing of the fragments 4 when secured to the stem part 1.

Depending on the application, other fasteners similar or equivalent to the aforementioned screws 24 may be used instead, such as nails, rivets, clips or staples. Similar features apply to these other fasteners than the screws.

Preferably, the fasteners are at least partially rigid. In particular, the term "fastener" does not refer to a suture per se. The fasteners may although comprise a wire or a suture: when such wire or suture is foreseen, the fastener further comprises at least one rigid part.

Although not shown on the figures, the internal part 22 may comprise barbs formed integrally. The term "barbs" may for example refer to spikes or claws. Thus, the barbs may contribute to better securing of the fragments 4 to the stem part 1. These barbs advantageously protrude out of the gap 9, at the periphery of the stem part 1. The barbs preferably protrude outwardly from the internal part 22. The barbs preferably protrude in a direction radial to the axis X1 or slightly inclined relative to such a direction.

In the embodiment of FIG. 3, an internal part 32, that may otherwise have the same features than the internal part 22 described above for the embodiment of FIGS. 1 and 2, further comprises one or more elastic tongues 34, elastic protrusions, and/or notches 36, or similar clipping means. In this case, the implant of the prosthesis P comprises the internal part 32 instead of the internal part 22. Thus, the internal part 32 may be secured to the stem part 1 by snap-fitting or clipping to the stem part 1 within the gap 9. Advantageously, the internal part 32 may also be unclipped from the stem part 1. For enabling snap-fitting or clipping of the internal part 32, the gap 9 is optionally provided with protrusions or notches interacting with the protrusions or notches of the internal part 32. With this embodiment, positioning of the implant is made very easy and is particularly reliable.

Figure 4:
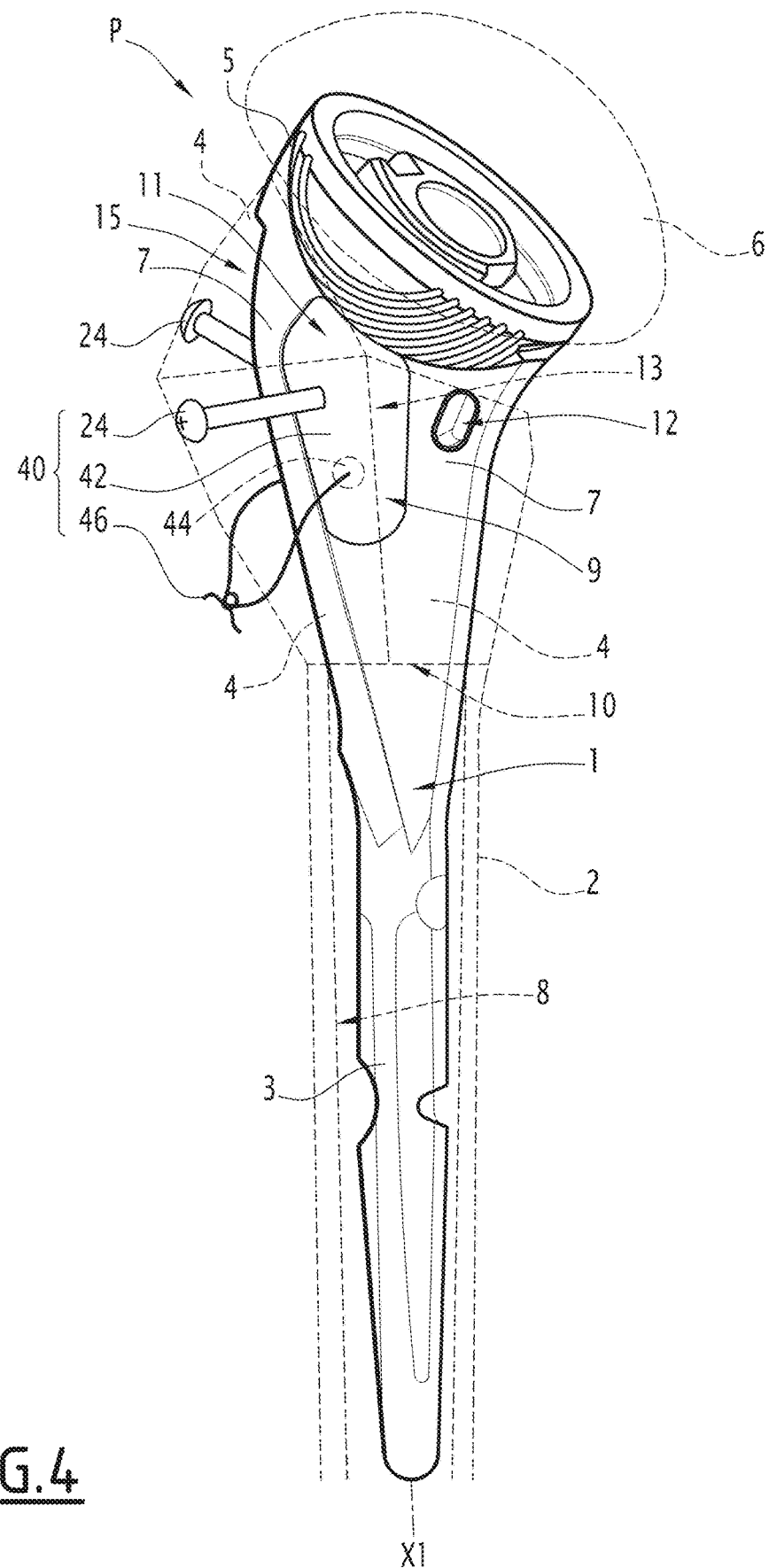
FIG. 4 is a schematic perspective view of a prosthesis according to another embodiment of the invention.

Turning now to FIG. 4, an implant 40 comprises fasteners, preferably screws 24, and an internal part 42, that may otherwise have the same features than the internal parts 22 and/or 32. The internal part 42 receives two fasteners 24 for securing the epiphyseal fragments 4. In this case, the implant 40 of the prosthesis P comprises the internal part 42 instead of the internal part 22. In addition to the fasteners 24, the internal part 42 receives one or more anchors 44. Each anchor 44 is implanted into the internal part 42, so that the anchor is secured to said internal part 42, preferably fixedly relative to said internal part 42. A suture 46 for securing one or more of the fragments 4 may be attached to the anchor 44. With this embodiment, the advantages of sutures are combined with the advantages of fasteners. Thus, depending on the situation, the position of the anchor may be adapted for improving securing with the sutures 46, without modifying the stem part 1.

Figure 5:
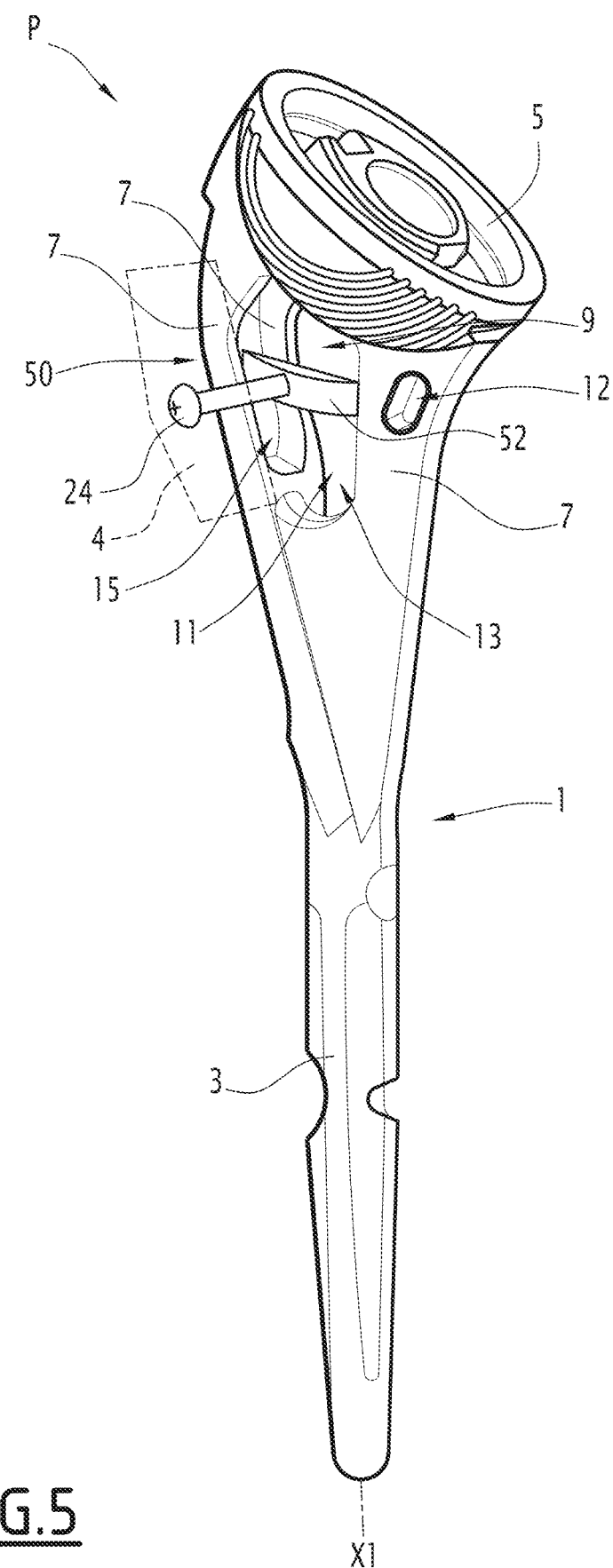
FIG. 5 is a schematic perspective view of a prosthesis according to another embodiment of the invention.

In the embodiment of FIG. 5, the implant 50 comprises one screw 24 and an expansible body 52 constituting an internal part.

In non-shown embodiments, the implant 50 may comprise more than one screw 24 and more than one distinct expansible bodies 52, the expansible bodies forming the internal part of the implant. Preferably, one expansible body is provided for each screw 24. Thus, for this not shown embodiment, the internal part may be constituted of a plurality of distinct expansible bodies, while in the other above-mentioned embodiments, the internal part is preferably constituted of only one piece, preferably an integral body, or several pieces fixedly attached together.

In the present case, the screw 24 is screwed to the expansible body, through a threaded hole thereof. This expansible body has a radially retracted configuration, allowing insertion of the expansible body into the gap through one of the openings 11, 13 or 15. "Radially" means a direction radial relative to the rotation axis of the screw 24. The expansible body also has a radially expanded configuration preventing extraction of the expansible body from the gap 9. Practically, when the expansible body is positioned within the gap 9 in expanded configuration as depicted in FIG. 5, the expansible body is blocked by the legs 7 and thus cannot be extracted from the gap 9 by pulling the screw 24 by the head. Thus, in expanded configuration, the expansible body is secured to the stem part 1. Preferably, the expansible body is put in the expanded configuration by securing the screw 24 thereto. In the present case, turning the screw 24 in a specific direction of rotation while said screw 24 is in the threaded opening of the expansible body mechanically expands said expansible body. Turning the screw 24 in the opposite direction of rotation may retract the expansible body. Thus, the expansion of the expansible body may be controlled by the surgeon. The surgeon may introduce the expansible body into the gap 9 through one of the openings 11, 13 or 15 while the expansible body is in the retracted configuration. Then, the surgeon may turn the screw 24 so that the expansible body is put to expanded configuration.

For example, the expansible body may be an expansible plug, an expansible bolt or an expansible anchor. The screw and the expansible body may together constitute a sleeve anchor bolt.

In an embodiment not shown on the drawings, the implant may comprise an internal part comprising at least one expansible body and at least one fastener as disclosed above, and at least one exterior part secured to the internal part by means of the fastener.

Figure 6:
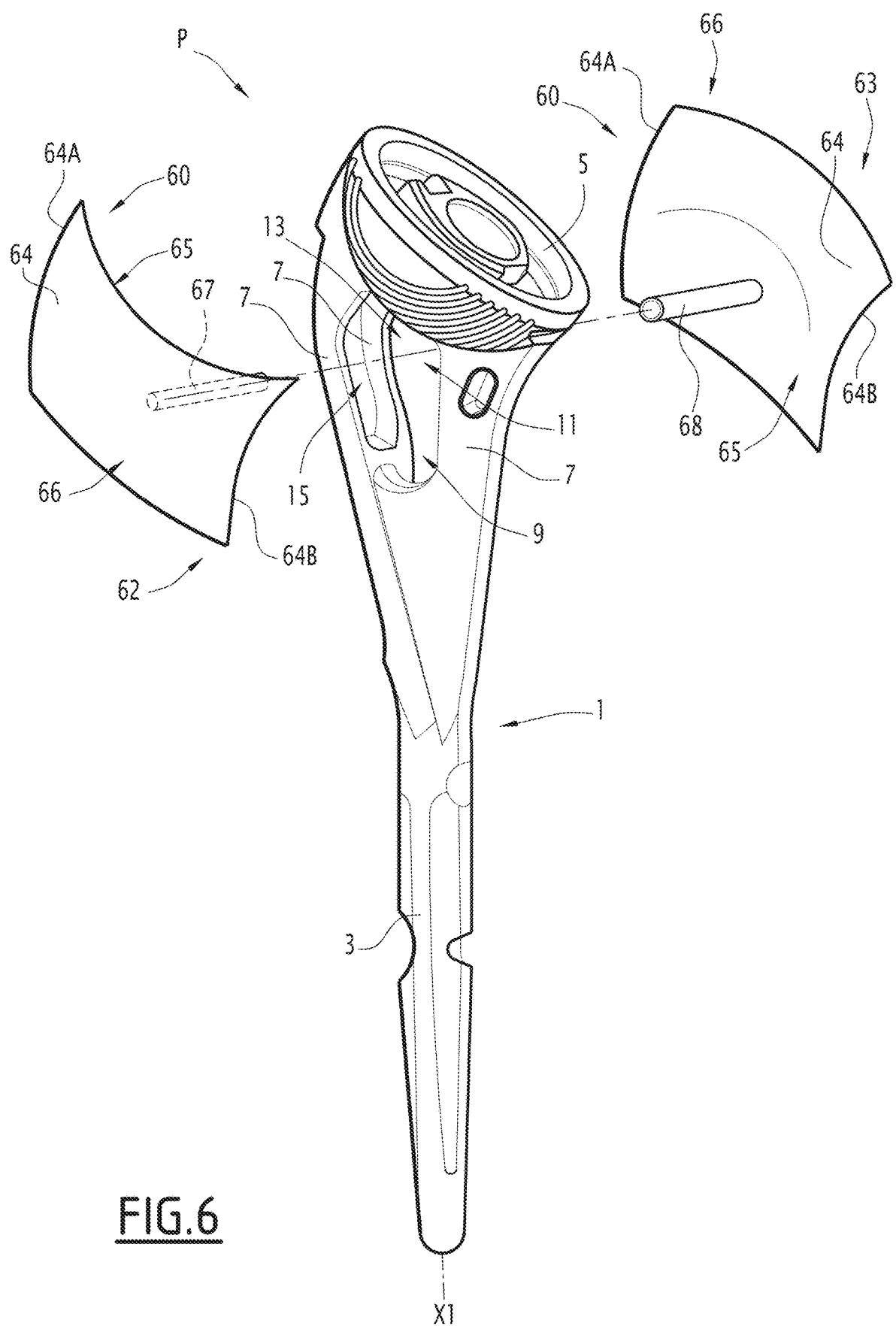
FIG. 6 is a schematic perspective exploded view of a prosthesis according to another embodiment of the invention.

Turning now to FIG. 6, an implant 60 comprises two exterior parts 62 and 63. The phrase "exterior part" preferably means that the parts 62 and 63 essentially extend outside from the gap 9, in the surroundings of the stem part 1. Each part 62 and 63 is configured to be secured to the stem part 1.

Each part 62 or 63 comprises a pad 64. When the parts 62 and 63 are mounted onto the stem part 1, the pads 64 wrap the stem part 1 around axis X1, at the height of the gap 9 and/or of the epiphyseal end 5. In other words, the parts 62 and 63 have a respective pad 64 located at the periphery of the stem part 1. Each pad 64 is preferably shaped as a curved leaf or a curved part, turning around axis X1 when the concerned part 62 or 63 is mounted onto the stem part 1. The curved leaf or part is preferably generally rectangular, as illustrated on FIG. 6. For example, the pad 64 may be hemi-conical, hemispherical or hemi-cylindrical. Preferably, when mounted, each pad 64 covers a minimum of 100° of the perimeter of the stem part 1, around axis X1. Each pad 64 may cover 180° of the stem part, so that the stem part 1 is covered at 360° around axis X1 by the two pads 64 when they are mounted.

Preferably, when mounted, an internal curved surface 65 of the pad 64, directed towards the stem part 1, is at least partially in contact with the stem part 1. In the present example, each pad 64 is located along one or two of the linker legs 7, in other words, each pad 64 covers one or two linker legs 7. In another aspect, at least a part of the shape of the internal curved surface 65 is preferably of corresponding or mating shape with the stem part 1.

Preferably, when mounted, each pad 64 at least partially covers one of the openings 11 and 13. In the present example, the openings 11 and 13 are totally covered respectively by the two pads 64.

Each pad 64 is centered onto one of the openings 11 and 13. Each pad 64 has two peripheral ends 64A and 64B. The ends 64A are preferably in contact with each other when the exterior parts 62 and 63 are mounted, or at least at close proximity. When mounted, the ends 64A preferably cover the opening 15. The ends 64B are preferably in contact with each other when the exterior parts 62 and 63 are mounted, or at least at close proximity. When mounted, the ends 64B preferably cover one of the legs 7 opposed to the opening 15.

In a non-represented embodiment, a first pad may have a first material and the second pad a second material, the first and the second material being different from each other.

A different material may be chosen for one of the pads 64 than for the other.

The pads 64 may be made specifically to a patient, namely be patient-specific. The pads 64 may be obtained by additive manufacturing.

Each pad 64 may receive one or more epiphyseal fragments 4 on an external surface 66 of the pad 64. The epiphyseal fragment 4 may be positioned along and against said external surface 66 for being secured to the pad 64. For example, the epiphyseal fragments may each be a tuberosity of the fractured bone, to be reattached. One pad 64 may receive the lesser tuberosity, while the other pad 64 may receive the greater tuberosity.

Thanks to the parts 62 and 63 that may be secured to the stem part 1, a single stem part 1 can be adapted for different situations, by securing different kinds of exterior parts like parts 62 and 63 thereto. In particular, appropriate exterior part may be chosen or made depending on the category of the patient, or the pathology to be treated, or even specifically to a particular patient, while the stem part 1 is a standard component. The epiphyseal fragment 4 may be secured to the exterior parts before said exterior parts are secured to the stem part 1, which enables easier surgery.

The exterior parts 62 and 63 are specifically adapted to the case where the epiphyseal fragments are very thin or in poor condition. The pads 64 may indeed mechanically support and reinforce these fragile fragments, so that they may be safely reintroduced into the patient's body, for a better healing of the patient.

Alternatively, one or more of the pads may be shaped so as to replace one or more of the epiphyseal fragments, for example when said fragment is not viable.

Each pad 64 may be provided with through-holes for receiving sutures for securing the fragment 4 against said pad 64. Each suture through-hole may be provided from surface 66 to surface 65. Alternatively or additionally, each pad 64 may be provided with holes for securing fasteners such as screws through said pad 64. Each fastener through-hole may be provided from surface 66 to surface 65. Alternatively or additionally, the pads 64 may be provided with holes or pores promoting bone ingrowth therethrough. These holes are preferably macroscopic, for example superior to 0.5 mm (millimeters). Instead, smaller holes or porosities may be provided for a similar effect, depending on the application.

In a non-represented embodiment, one or both pads may comprise barbs formed integrally with the concerned pad. The barbs may contribute to better securing of the fragments 4 to the concerned pad. The barbs preferably protrude outwardly from the pad. The barbs preferably protrude in a direction radial to the axis X1 or slightly inclined relative to such a direction.

The implant 60 is secured to the stem part 1 through the gap 9. In the case of FIG. 6, the exterior part 62 comprises an arm 67, while the exterior part 63 comprises an arm 68. Both arms 67 and 68 protrude from the internal surface 65 of the concerned part 62 or 63. The arms 67 and 68 are configured to be coaxial when the parts 67 and 68 are secured to the stem part 1. Each arm 67 and 68 is preferably oriented radially to the axis X1, or at least, perpendicular to said axis X1. The arm 67 is inserted into the gap 9 through the opening 11, while the arm 68 is inserted into the gap 9 through the opening 13. One or more of the exterior parts may be secured through other holes leading to the gap 9 and delineated by the legs 7, such as the opening 15. One of the arms 67 and 68 may have a tubular shape for axially inserting the other arm into this arm. The arms 67 and 68 may be snap-fitted together for fixedly securing the parts 62 and 63 relative to each other. When the parts 62 and 63 are secured this way, they are also secured to the stem part 1 thanks to the shape of the internal surfaces 65, corresponding to the peripheral shape of the stem part 1.

More generally, in the embodiment of FIG. 6, the part 62 constitutes a primary exterior part, the part 63 constitute a secondary part, the arm 67 constitutes a primary fastener and the arm 68 a secondary fastener, said primary and secondary fasteners being complementary. The primary fastener 67 is configured to cooperate with the secondary fastener 68 for fixing the primary exterior part 62 to the secondary exterior part 63. In other words, parts 62 and 63 are secured to each other by means of the fasteners 67 and 68, so as to be mechanically secured to the stem part 1, said stem part 1 being captured between the pads 64. Thus, the implant 60 is very easy to secure to the stem part 1.

In an alternative embodiment, the implant 60 may comprise more than two exterior parts.

Figure 7:
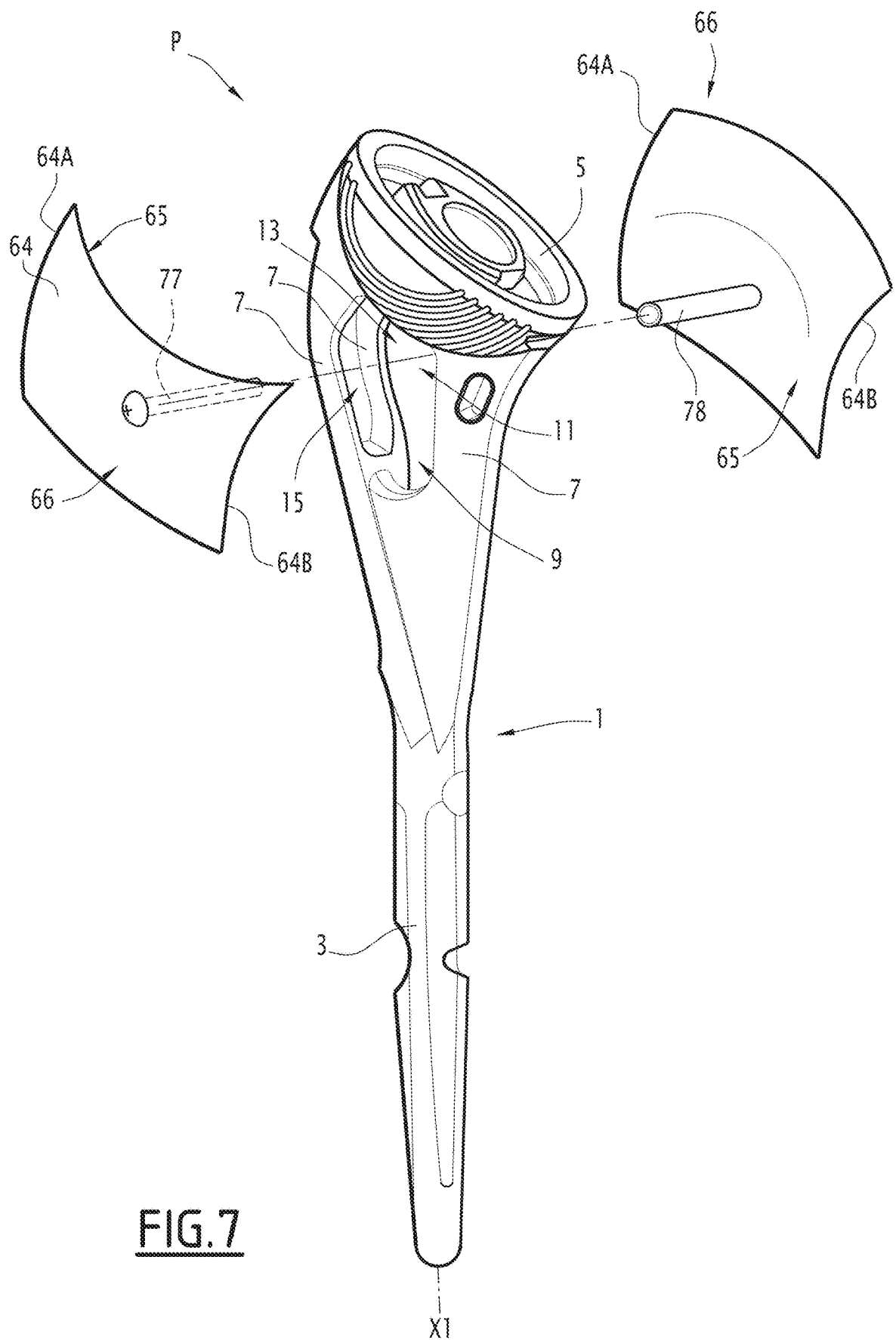
FIG. 7 is a schematic perspective exploded view of a prosthesis according to another embodiment of the invention.

Turning now to FIG. 7, the arms 67 and 68 of FIG. 6 have been replaced by another type of fasteners. The arm 67 is replaced by a screw 77 and the arm 68 is replaced by an internally-threaded tube 78, for the fastener 77 to be secured to the tube 78, preferably by screwing the screw in the threaded tube. The other features of the implant disclosed on FIG. 6 apply to the embodiment of FIG. 7.

Figure 8:
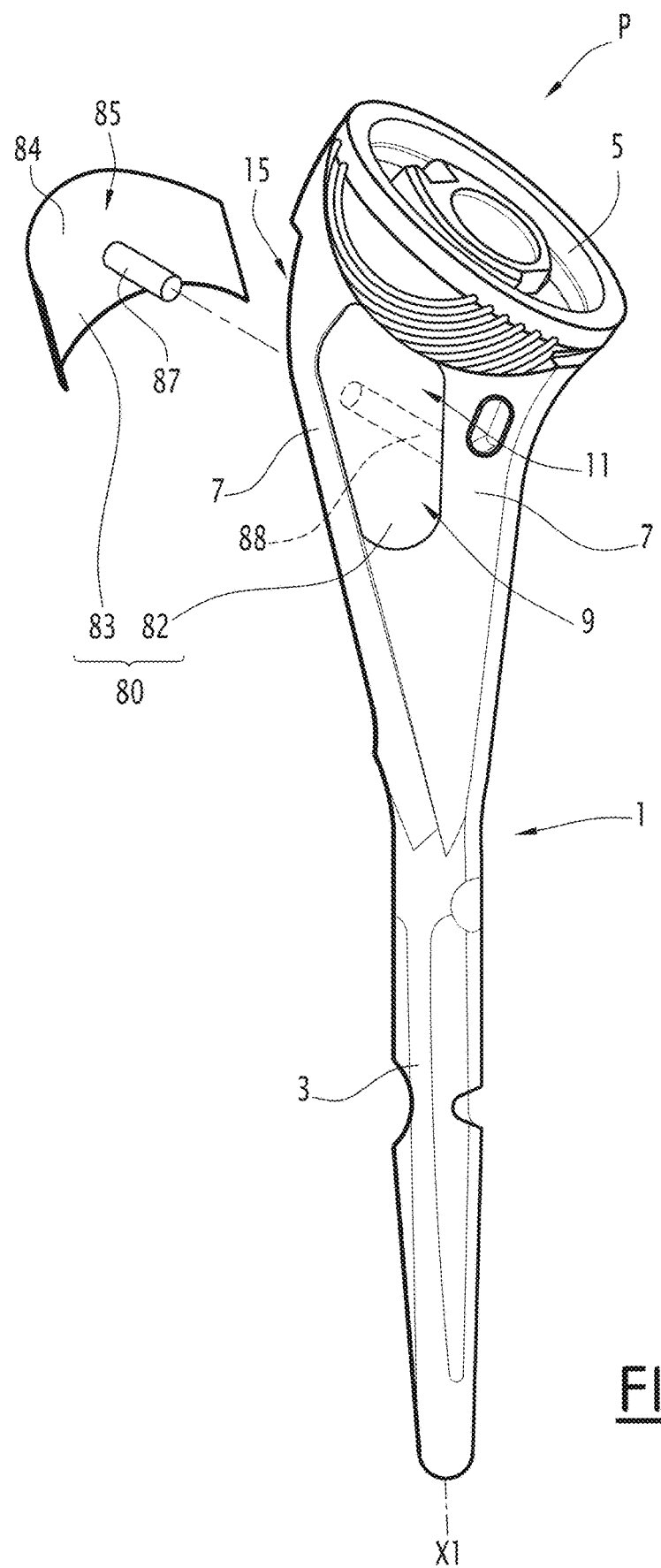
FIG. 8 is a schematic perspective exploded view of a prosthesis according to another embodiment of the invention.

In the embodiment of FIG. 8, an implant 80 comprises an internal part 82 that may have the same features as the internal parts disclosed above, especially the internal part 22.

The implant 80 also comprises an exterior part 83, distinct from the internal part 82. The exterior part 83 may have the same features than the exterior part 62 or 63 disclosed above and in FIG. 6 or 7. In the case of FIG. 8, the exterior part has an arm or a fastener 87, protruding from the internal surface 85 of the pad 84, and is secured into a receiving hole 88 of the internal part 82. This securing is preferably obtained by snap-fitting the arm 87 within the hole 88. Other modes of securing may be provided, such as screwing or force-fitting.

Similar to the above-mentioned pads 64, the pad 84 of the present example has a rectangular shape, and is curved around the stem part 1, around axis X1.

In the case of FIG. 8, the implant 80 combines the advantages of the internal parts and of the exterior parts mentioned above.

In the case of FIG. 8, the exterior part 83 is secured to the internal part 82, the arm 87 passing through the opening 15. In an alternative embodiment, the exterior part 83 may be secured through any other of the holes delineated by the legs 7. The implant 80 may comprise more than one exterior parts secured to the internal part through a respective opening 11, 13 or 15. In the present example, the pad 84 totally covers the opening 15. The opening 15 may be covered only partially instead. The openings 11 and 13 are however not completely covered by the pad 84, or even left entirely free.

Figure 9:
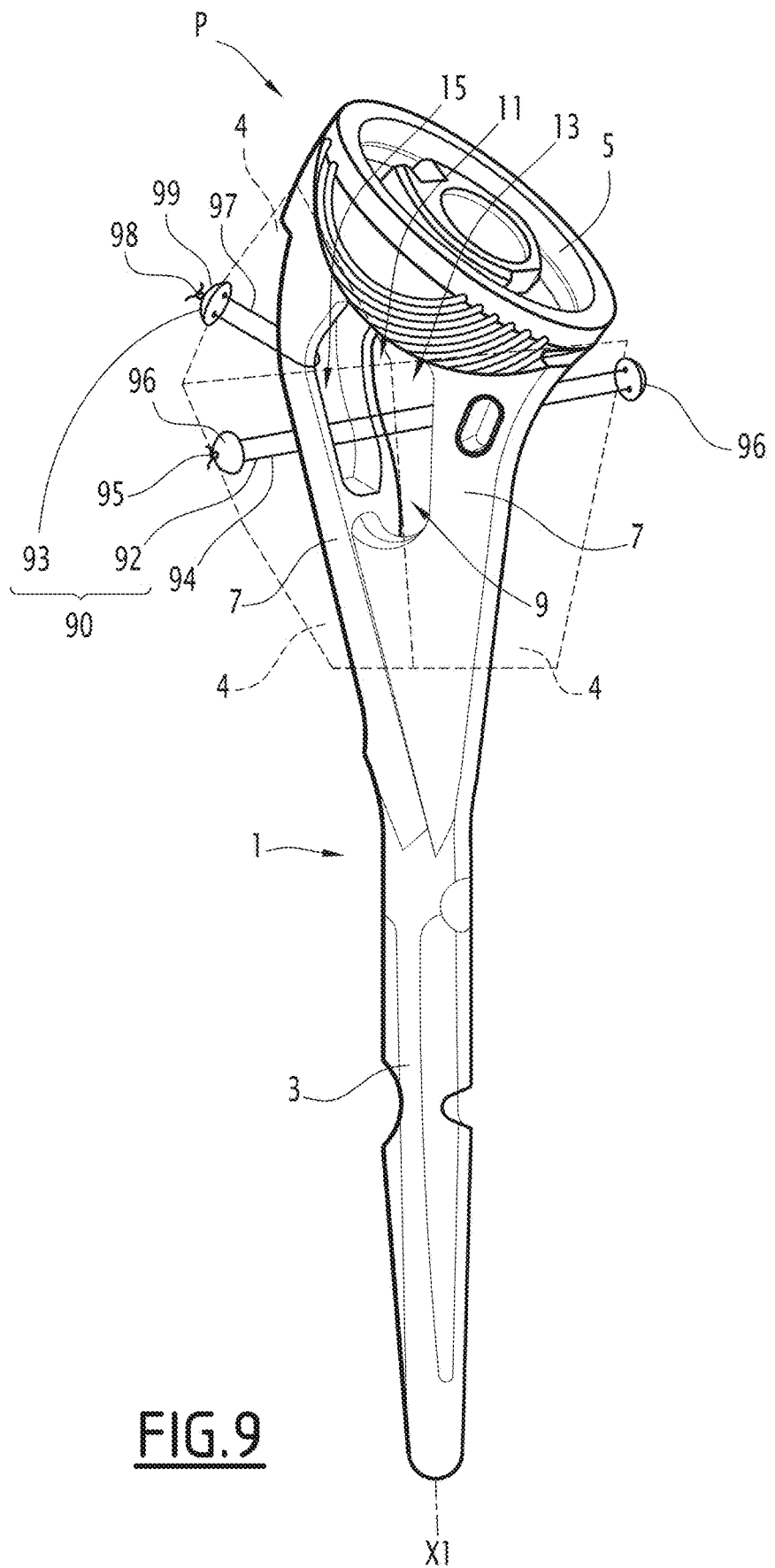
FIG. 9 is a schematic perspective view of a prosthesis according to another embodiment of the invention.

Turning now to FIG. 9, the stem part 1 is provided with an implant 90 comprising one or more exterior parts 92. Each exterior part 92 comprises one or more yarns or threads 94, each yarn forming a loop. Each yarn 94 may have a knot 95 for closing the loop. Each yarn 94 is arranged so as to circle around at least one of the linker legs 7, or at least so as to pass through the gap 9, by passing through at least two of the openings 11, 13 and 15. In the present case, the yarn 94 passes through openings 15 and 13. Each yarn 94 bears at least one button 96, preferably two buttons 96. The buttons 96 are positioned at the periphery of the gap 9, at the height of the linker legs 7 along axis X1. The buttons 96 are preferably arranged at the opposite of the loop formed by the yarn 94. The yarn 94 is preferably tensioned, so as to tend to bring the buttons 96 towards each other. One or more epiphyseal fragments 4 may be interposed between a first button 96 and the stem part 1. With tension of the yarn 94, these fragments 4 are secured to the stem part 1, as they are caught between the button 96 and the stem part 1. Preferably, the concerned fragments 4 are arranged along the linker legs 7 and/or along the epiphyseal end 5 of the stem part 1. One or more further epiphyseal fragments 4 may be interposed between a second button 96 and the stem part 1. These further fragments 4 are thus caught between the second button 96 and radially opposite side of the stem part 1, compared to the first button 96, as depicted on FIG. 9. The yarn 94 preferably passes through the attached fragments 4. For particular applications, one of the buttons 96 may be omitted, one of the fragments 4 being interposed between a portion of the yarn 94 and the stem part 1, alike for a suture.

Additionally or alternatively to the exterior part 92, the implant 90 may comprise one or more exterior parts 93. Each exterior part 93 comprises one or more yarns 97, each yarn forming a loop. Each yarn 97 may have a knot 98 for closing the loop. Each yarn 97 is arranged so as to circle around at least one of the linker legs 7. In the present case, the yarn 94 passes through openings 11 and 15, circling one of the legs 7. Each yarn 97 bears at least one button 99, preferably only one button 99. The button 99 is positioned at the periphery of the gap 9, at the height of the linker legs 7 along axis X1. The yarn 97 is preferably tensioned, so as to tend to bring the button 99 towards the leg 7 to which the yarn is attached to. One or more epiphyseal fragments 4 may be interposed between the button 99 and the leg. With tension of the yarn 97, these fragments 4 are secured to the stem part 1, as they are caught between the button 99 and the leg 7. Thus, the concerned fragments 4 are arranged along the linker leg 7 and/or along the epiphyseal end 5 of the stem part 1. The yarn 97 preferably passes through the attached fragments 4.

For attaching the fragments 4, the surgeon may position said fragments 4 along the stem part 1, pass the yarn through said fragments 4, including also positioning the buttons on the fragments 4. The surgeons may the tie the knot 95 or 98 to form the loop with the yarn 94 or 97. Once the loop is formed, the surgeon may activate a tensioner integrated to of one of the buttons 96 or 99, so as to tension the yarn 94 or 97 passed through. The tensioner of the button 96 or 99 is preferably a mechanical tensioner. For example, the tensioner function of a button may be obtained by an expansible button, the knot 95 or 98 being tied as the button is in a retracted configuration, the surgeon then toggling the button to an expanded configuration so as to mechanically tense the yarn.

Figure 10:
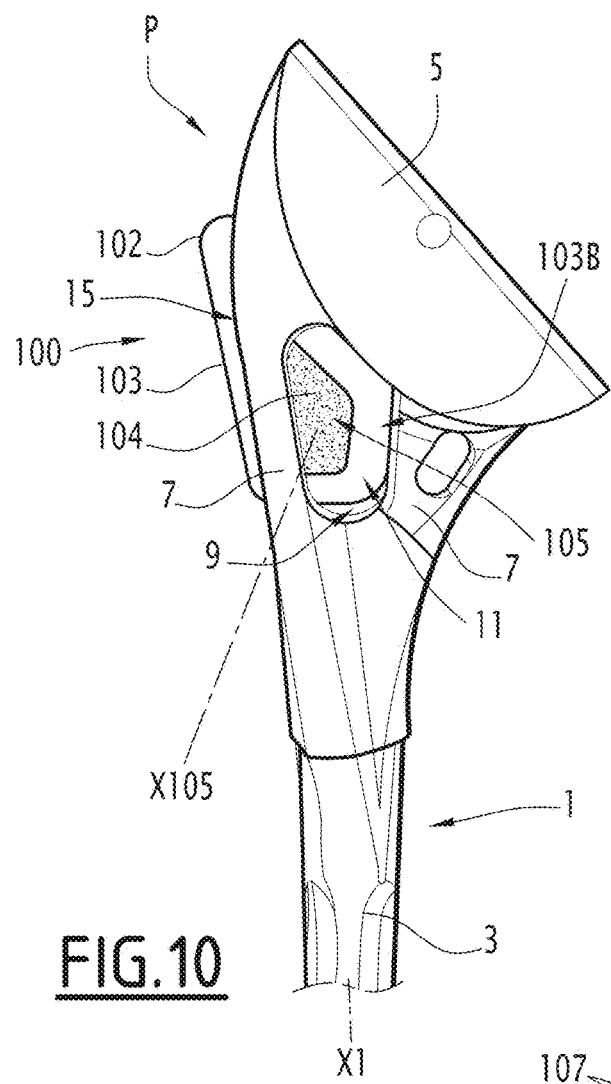
FIG. 10 is a schematic perspective view of a prosthesis according to another embodiment of the invention.
Figure 11:
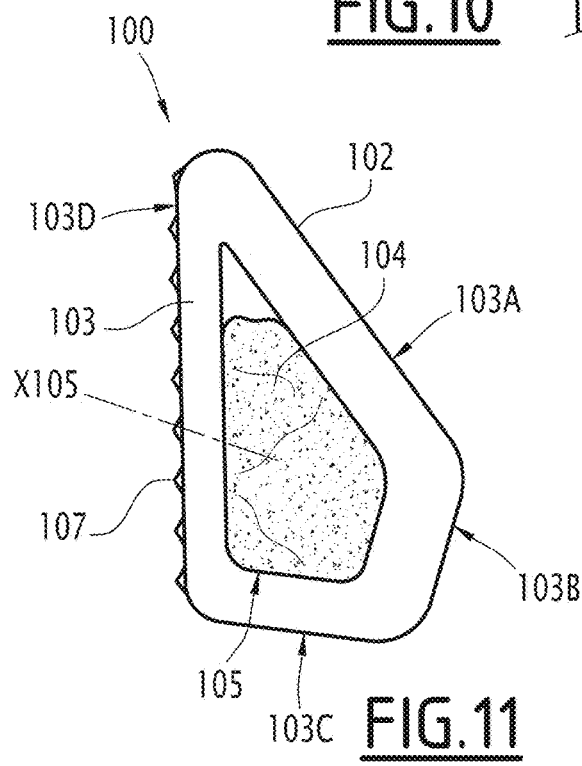
FIGS. 11 and 12 are schematic perspective views of an implant of the prosthesis of FIG. 10, under two different orientations.
Figure 12:
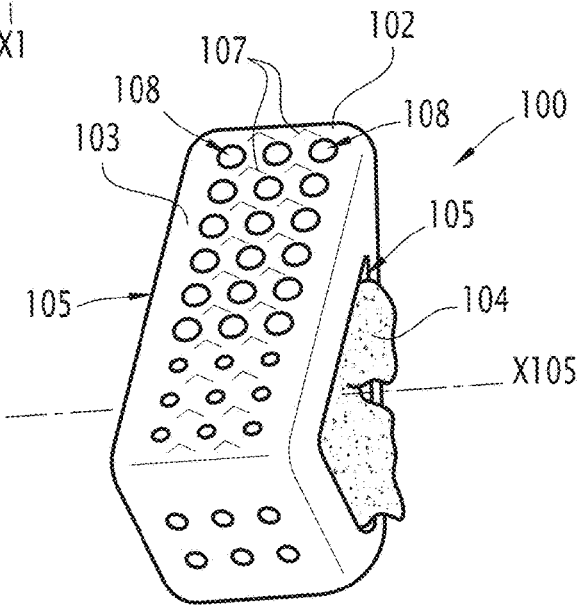

In the embodiment of FIGS. 10, 11 and 12, an implant 100 comprises an internal part 102, preferably having the features mentioned for the above-disclosed other internal parts.

The internal part 102 differs from the other internal parts disclosed above in that the internal part 102 comprises a peripheral shell 103 and a core 104 received within the peripheral shell 103. Thus, in this case, the internal part 102 is not made of a single integral part, but at least of two distinct combined parts: the shell 103 and the core 104.

The shell 103 is preferably entirely positioned within the gap 9, between the legs 7 and between the rod 3 and the end 5. In some embodiments, as it is the case on FIG. 10, the shell 103, may partially extend out of the gap 9, for example through one or more of the openings 11, 13 and 15. In this case however, the shell 103 is preferably mostly enclosed within the gap 9. In FIG. 10, the shell extends out of the gap 9, passing through the opening 15.

The shell 103 is preferably made of one integral part, in other words a single piece. The shell 103 is preferably made of a material softer than the material of the stem part 1.

The material of the shell 103 is preferably as defined above for the internal part 22 and for the pad 64.

In a most preferred embodiment, the shell 103 comprises the biologic material defined above. The shell 203 may also comprise degradable and non-degradable materials. For example, degradable materials may include, but are not limited to polyesters, polyanhydrides, polyurethanes, and polysaccharides. Alternatively, the material may be one of the materials defined above.

Preferably, the shell 103 is shaped corresponding to the shape of the gap 9, so that the internal part 102 may be fitted into the gap 9.

Preferably, the shell 103 is mounted into the gap 9 through the opening 15. Preferably, the shell 103 is mounted with force-fitting.

In another embodiment, the shell 103 may be secured to the stem part 1 by snap-fitting or clipping to the stem part 1 within the gap 9. Advantageously, the shell 103 may also be unclipped from the stem part 1. For enabling snap-fitting or clipping of the shell 103, the gap 9 is optionally provided with protrusions or notches interacting with the protrusions or notches of the shell 103. With this embodiment, positioning of the shell 103 within the gap 9 is made very easy and is particularly reliable.

The shell 103 may be made specifically to a patient, namely be patient-specific. The shell 103 may be obtained by additive manufacturing.

An internal part 102 including a shell 103, of desired shape may be implemented to the stem part 1 for adapting the prosthesis P to different applications. For example, a left shoulder and a right shoulder prosthesis may be obtained with a stem part of the same reference, by combining said stem part with an implant specific to a right shoulder or an implant specific to a left shoulder. Thus, fewer references of stem parts are necessary.

The shell 103 comprises a cavity or a hole for housing the core 104. Preferably, the cavity has at least one opening 105 through which a surgeon may position the core 104 within the cavity of the shell 103. In the illustrated example, two opposite openings 105 are provided, although only one is visible on FIGS. 10 and 11. Preferably, as it is the case in FIG. 10, each opening 105 is at least partially obstructed by one or more of the legs 7 when the internal part 102 is positioned in the gap 9, so that the core 104 may not migrate out of the cavity of the shell 103 when the implant 100 is positioned within said gap 9. Preferably, in this situation, the opening 105 is not entirely obstructed so that the core 104 is in contact with tissues or fluids of the body of the patient when the prosthesis P is implanted in the patient.

In the example depicted on FIGS. 10, 11 and 12, the shell 103 has a prismatic shape with a trapezoid base. The openings 105 are provided at either bases of the prismatic shape. The openings 105 and the cavity of the shell 103 may be considered as a through-opening of the shell 103 along an axis X105, in which the core 104 is contained. The axis X105 is intended to be perpendicular to the axis X1.

The shell 103 of the present example has four peripheral surfaces 103A, 103B and 103C and 103D, surrounding the openings 105, parallel to the axis X105.

When the implant 100 is secured to the gap 9, at least two, preferably all, of the surfaces 103A, 103B and 103C bear against three respective inner walls of the gap 9. The surface 103B may bear against the inner wall formed by one of the legs 7, said leg 7 being opposed to the opening 15. The surface 103A, adjacent to the surface 103B, may bear against the inner wall formed by the epiphyseal end 5. The surface 103C, adjacent to the surface 103B and opposed to the surface 103A, may bear against the inner wall formed by the rod 3. The surface 103D, adjacent to surfaces 103A and 103C and opposed to surface 103B, extends so as to fill the opening 15. Preferably, surfaces 103A and 103B may extend parallel, or with a slightly inclined angle, relative to axis X1, while surfaces 103A and 103C are transverse.

The surface 103D may extend outside from the gap 9 along two of the legs 7 surrounding the opening 15, as visible on FIG. 10. Thus, surface 103D may constitute an exterior surface of the shell 103.

The shape of the shell 103, including the surfaces 103A, 103B, 103C and 103D, may apply to the internal part 22 of FIGS. 1 and 2, although the internal part 22 is devoid of through opening like the openings 105.

The core 104 preferably comprises bone graft. Preferably, the bone graft of the core 104 is autogenous bone graft, for example formed at least partially with the initial head of the long bone to which the prosthesis P is added. The bone graft may also be autogenous iliac bone graft. Any other type of bone graft may be used depending on the application.

Since the bone graft core 104 is received within the shell 103, the internal part 102 combines the advantages of having a bone graft, which may allow better healing of the patient, while having a very precise shape, provided by the shape of the shell 103. For being introduced into the shell 103, the bone graft core 104 does not need to have a very precise shape, which may save time, especially in the case of an autogenous bone graft, which may be extracted and recut during the surgery. Thus, the internal part 102 is very easy to mount and to secure to the stem part 1 so that surgery is made easier.

As visible on FIG. 12, series of holes 108, smaller than the openings 105, may be provided on one or more of the surfaces 103A, 103B, 103C and 103D, for promoting bone ingrowth. Each concerned surface 103A, 103B, 103C and 103D may have several of these holes 108. Each of these holes may lead into the inner cavity of the shell 103.

As visible on FIGS. 11 and 12, the shell optionally comprises barbs 107, provided on the surface 103D, which is exterior. The surface 103D may be used for securing epiphyseal bone fragments.

Figure 13:
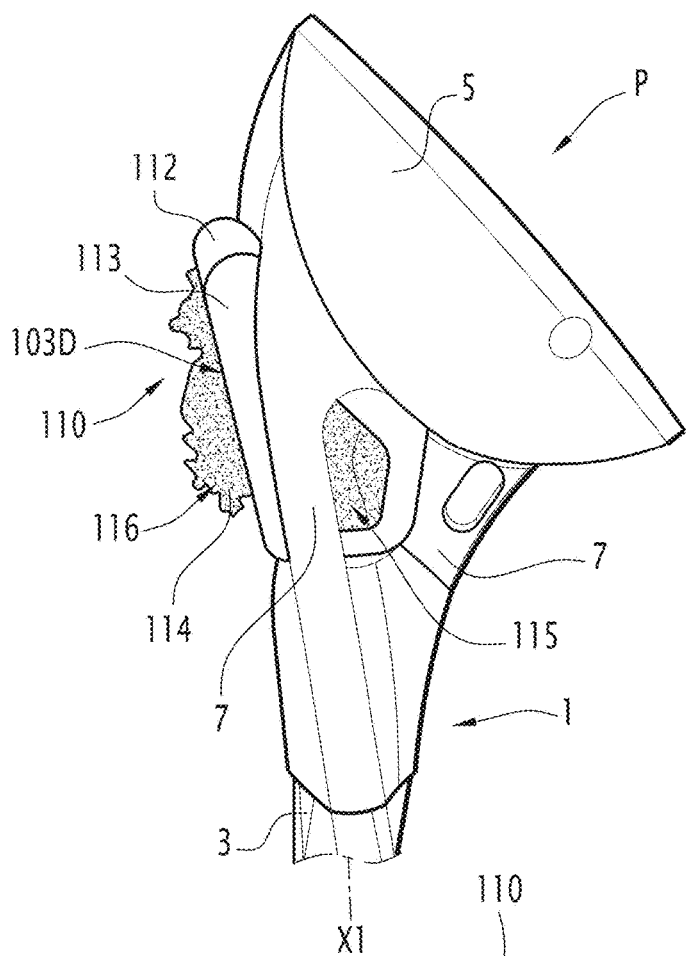
FIG. 13 is a schematic perspective view of a prosthesis according to another embodiment of the invention.
Figures 14, 15, 16:
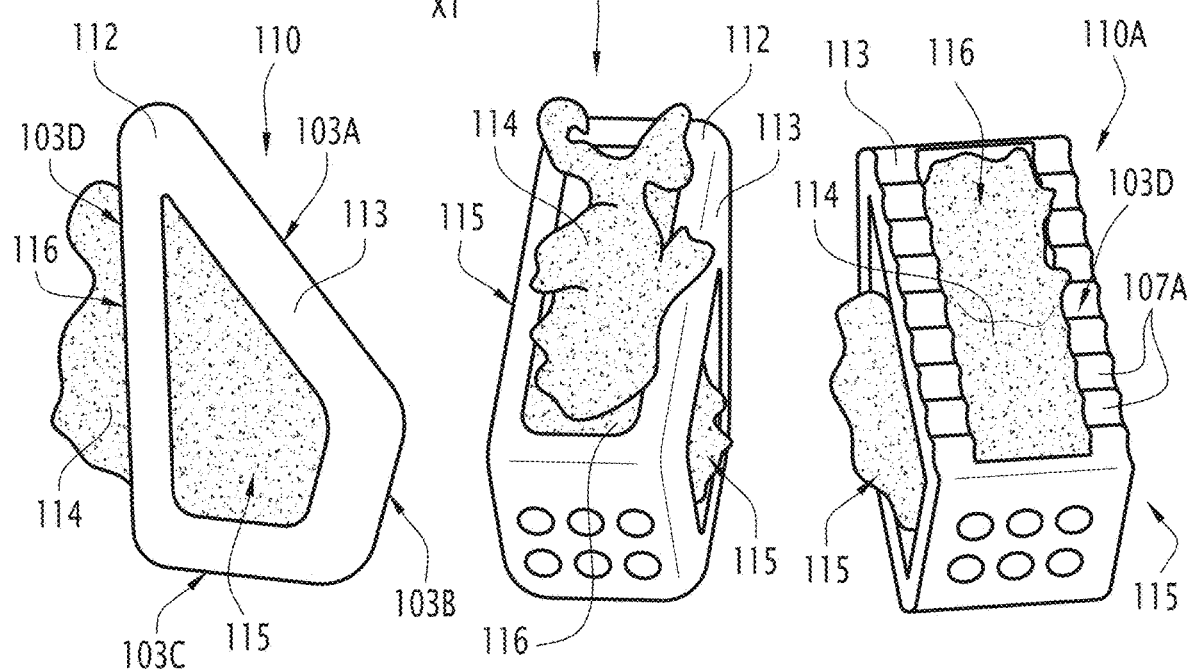
FIGS. 14 and 15 are schematic perspective views of an implant of the prosthesis of FIG. 13, under two different orientations.
FIG. 16 is a schematic perspective view of an implant for a prosthesis according to another embodiment of the invention.

FIGS. 13, 14 and 15 depict another embodiment, where an implant 110 essentially has the same features than the implant 100 and some differences explained below. In particular, the implant 110 comprises an internal part 112 including a shell 113 and a core 114 positioned within said shell 113. The shell 113 has one or two opposed openings 115 leading to the inner cavity, alike shell 103. Differently from shell 103, shell 113 comprises an opening 116, best visible on FIG. 15, leading to the inner cavity of the shell 113. The opening 116 is provided on a part of the shell 113 that protrudes outside of the gap 9, preferably through the opening 15 of the stem part 1. In the present case where the shell 113 has the same shame than the shell 103, the opening 116 is provided through the surface 103D, leading to the inner cavity of the shell 113. Thus, when the shell 113 is mounted within the gap 9, the opening 116 is not obstructed by any leg 7, as visible on FIG. 13. As depicted on FIGS. 13, 14 and 15, the bone graft core 114 may partially protrude out of the shell 113 through the opening 116. This may promote healing of the patient. In particular, one or more epiphyseal fragments may be secured against the protruding core 114.

In the example of FIGS. 13 to 15, the surface 103D is devoid of the abovementioned barbs 107 and holes 108.

In case the opening 116 is provided to the shell 113, the openings 115 are optional. Thus, the shell 113 may only have the opening 116 and no openings 115.

FIG. 16 depicts a further embodiment, where an implant 110A essentially has the same features than the implant 110 and some differences explained below. The implant 110A is shown on FIG. 16 with the same orientation than the implant 110 on FIG. 15. In the example of FIG. 16, contrary to the FIGS. 13 to 15, the surface 103D of the shell 113 is provided with barbs 107A, arranged so as to surround the opening 116A. FIGS. 17, 18 and 19 show an embodiment with a modified implant 120 compared to the implant 100. As implant 100, the implant 120 comprises an internal part 122, including a shell 123 and a core 124 positioned within said shell 123. The shell 123 has two opposed openings 125, through which the core 124 is positioned, and defining a transversal axis X125 of the shell 123, similarly to the openings 105 and the axis X105. The internal part 122 has the same features and shape than the internal part 102 disclosed above, as well as some differences explained below.

The implant 120 comprises an exterior part 127 secured to the shell 123. More precisely, the part 127 is secured to the surface 103D of the shell 123, or replaces the surface 103D. The exterior part 127 is preferably integral with said shell 123. Thus, the exterior part 127 may be considered as a part of the shell 123. The exterior part 127 is preferably made of the same material than the shell 123. One or more exterior parts similar to the part 127 may be provided for the implant 120.

"Exterior" preferably means that the part 127 essentially extends outside from the gap 9, in the surroundings of the stem part 1, alike parts 62 and 63, for example.

The exterior part 127 comprises a single pad. The pad of part 127 may have all the features of the pads 64 disclosed above. When the implant 120 is mounted onto the stem part 1 as shown on FIG. 17, the part 127 preferably extends along the stem part 1 around axis X1, at the height of the gap 9 and/or of the epiphyseal end 5. In other words, the part 127 is located at the periphery of the stem part 1.

In the illustrated example, the part 127 has a generally rectangular shape and is slightly curved around the axis X125 so as to match the shape of the stem part 1. The part 127 is preferably shaped as a curved leaf. In the present case, the part 127 extends along two of the legs 7, covering the opening 15, preferably totally. Preferably, the part 127 extends up to the proximal side of the epiphyseal end 5.

Preferably, the part 127 has a shape matching with the stem part 1. Preferably, the part 127 comprises a side 129 in contact with the stem part 1. The side 129 is preferably opposed to a side 124A of the part 127, oriented outwards. The part 127 preferably covers only a portion of the stem part 1 around axis X1.

One or more epiphyseal bone fragments may be secured to the stem part 1 so as to bear against the part 127.

Optionally, the part 127 may be provided with holes or through-holes 126, for example similar to the holes 108, for promoting bone ingrowth.

The exterior part 127 may comprise barbs 128 formed integrally. The barbs 128 preferably protrude outwardly, at the periphery of the stem part 1. These barbs 128 preferably protrude approximately radially relative to the axis X1. Thus, the barbs 128 may contribute to better securing of the fragments 4 to the stem part 1. In the present example, the barbs 128 are provided at the side 124A. In embodiments where no barbs are provided, the side 124A may be left bare.

More generally, the implant 120 may comprise barbs positioned along an exterior part formed integrally with the shell. Preferably, the barbs are positioned at an outer side of the shell and not in the internal cavity thereof. By "exterior part", it is meant that the exterior part is positioned essentially, or even totally outside from the gap 9.

FIGS. 20 to 23 show an implant 130 comprising an exterior part 131. The part 131 essentially extends outside from the gap 9, in the surroundings of the stem part 1.

Figure 20:
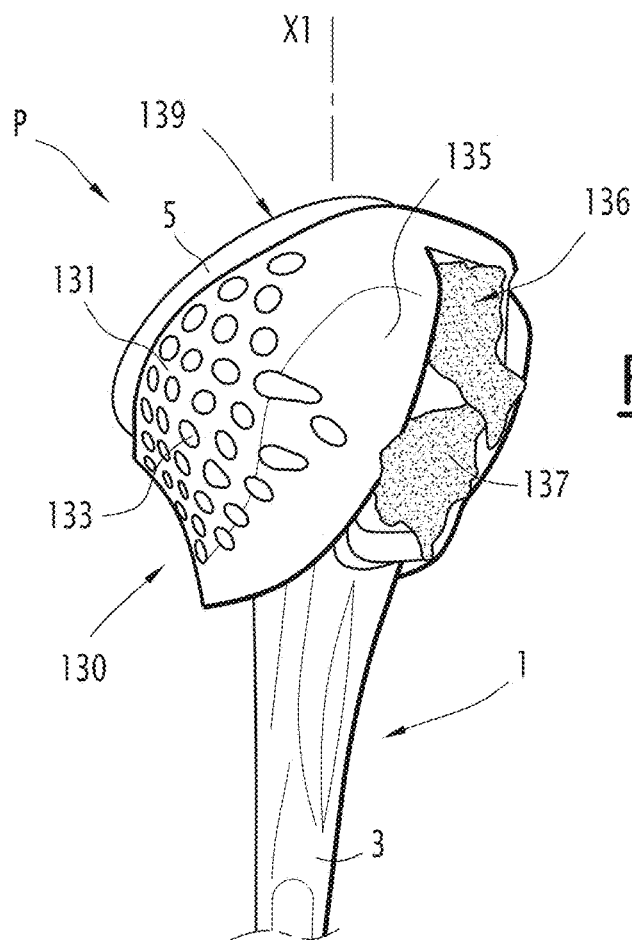
FIG. 20 is a schematic back perspective view of a prosthesis according to another embodiment of the invention.
Figure 21:
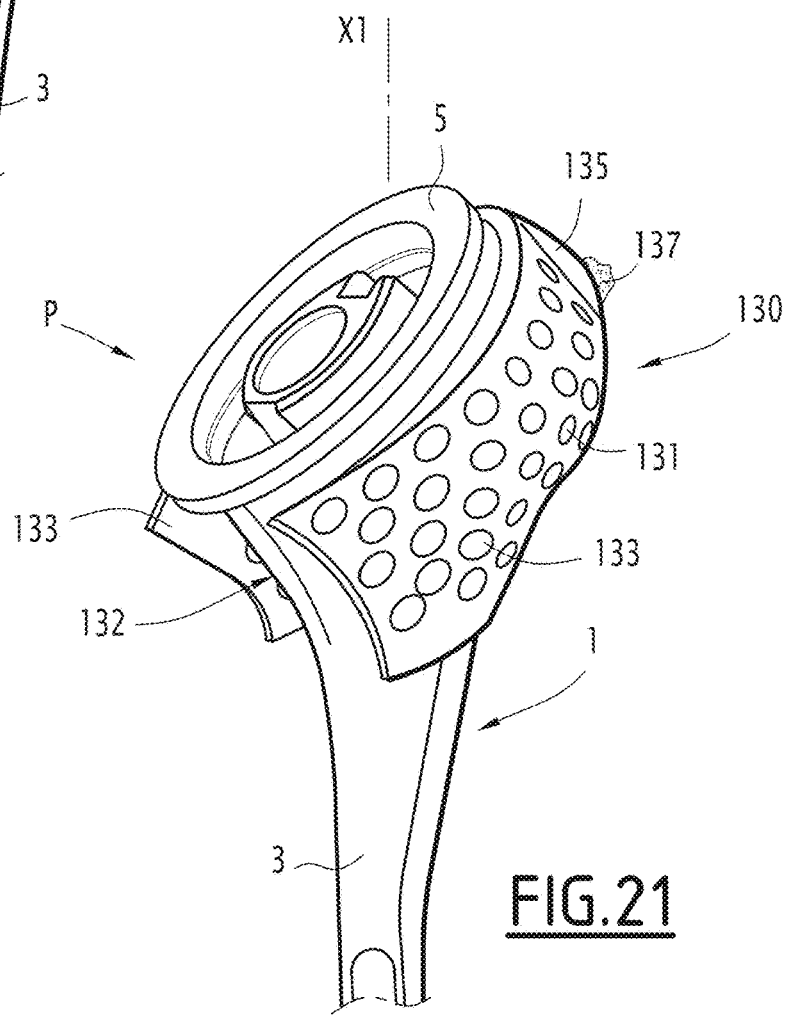
FIG. 21 is a schematic front perspective view of the prosthesis of FIG. 20.

The part 131 has a central body 135, located outside of the gap 9, covering the opening 15, when the part 131 is mounted onto the stem part 1 as shown on FIGS. 20 and 21.

The part 131 preferably has two wings 133, extending at either side of the central body 135 and both wrapping one side of the stem part 1 around axis X1. The wings 133 extend around the stem part 1, about axis X1. The openings 11 and 13 of the gap 9 are at least partially, preferably totally, covered by the wings 133. The wings 133 and the body 135 preferably wrap or recover the essential of the periphery of the stem part 1 around the axis X1. The wings 133 and the body 135 preferably extend up to the epiphyseal end 5 along axis X1, so as to cover the essential of its peripheral wall around axis X1.

Preferably, the part 131 only leaves a minor portion of the stem part 1 uncovered around axis X1, as visible in FIG. 21. At the opposite of the central body 135 around axis X1, the ends of the two wings 133 advantageously delineate an aperture 132, where one leg of the stem part 1 is at least partially apparent from the outside. Since the aperture 132 is provided, the stem part 1 is only partially wrapped by the part 131 around axis X1.

The exterior part 131 is configured to be secured to the stem part 1, the two wings 133 acting as positioners of the part 131 onto the stem part 1 along axis X1. The wings 133 and the body 135 advantageously define an axial through-opening 139 of the exterior part 131. The stem part 1 is located within this through-opening 139 when the part 131 is mounted thereon, the through-opening 139 extending parallel to the axis X1. In the embodiment of FIGS. 20 to 23, the through-opening is not exactly tubular, since the aperture 132 is provided all along said through opening.

Figure 22:
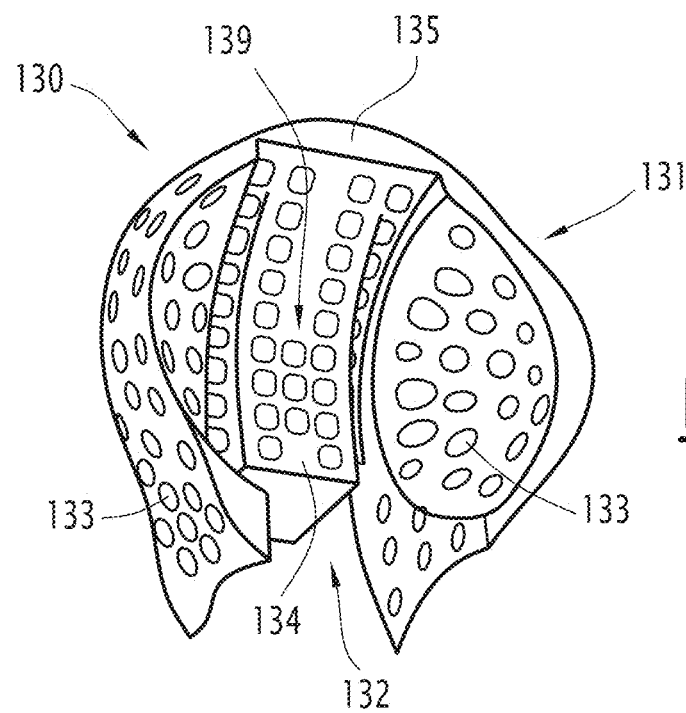
FIGS. 22 and 23 are schematic perspective views of an implant of the prosthesis of FIGS. 20 and 21, under two different orientations.

The exterior part 131 further comprises a rib 134, visible in FIG. 22, protruding from the central body 135, between the wings 133. The rib 134 protrudes within the opening 139. The rib 134 is preferably diametrically opposed to the aperture 132. As depicted on FIGS. 20 and 21, when the part 131 is mounted onto the stem part 1, the rib 134 is inserted within the gap 9 through the opening 15. The rib 134 may be formed so as to enable axial and rotational fixation of the part 131 relative to the stem part 1 and relative to axis X1, when the rib 134 is positioned within the opening 15.

For assembling the stem part 1 and the exterior part 131, the through-opening 139 is configured to enable axial insertion of the stem part 1 within the through-opening 139, putting the rod 3 first, and sliding along axis X1 until the end 5 axially abuts the wings 133 and/or the rib 134 is inserted within the opening 15 of the stem part 1. Thus, mounting the exterior part 131 is very convenient and may save surgery time.

Preferably, the body 135, the wings 133, and optionally the rib 134, form a single integral piece.

Preferably, the exterior part 131 comprises a peripheral shell, including at least the central body 135. Preferably, the peripheral shell also includes the wings 133 and the rib 134. The shell is shown separately from the rest of the prosthesis P on FIG. 21. The peripheral shell comprises an internal cavity, provided within the central body 135. As shown on FIG. 20, an opening 136 leading to the internal cavity is provided on the central body 135. This opening 136 is preferably directed radially outwards, for example opposed to the rib 134, so as to be accessible when the part 131 is mounted onto the stem part 1.

The internal cavity may house a core 137 of bone graft. Preferably, the core 137 of bone graft has the same features than the ones mentioned for the core 104 disclosed above. In the case of FIGS. 20 and 21, the core 137 may slightly protrude out from the opening 136 so as to promote securing of the epiphyseal fragments onto the prosthesis P.

Figure 23:
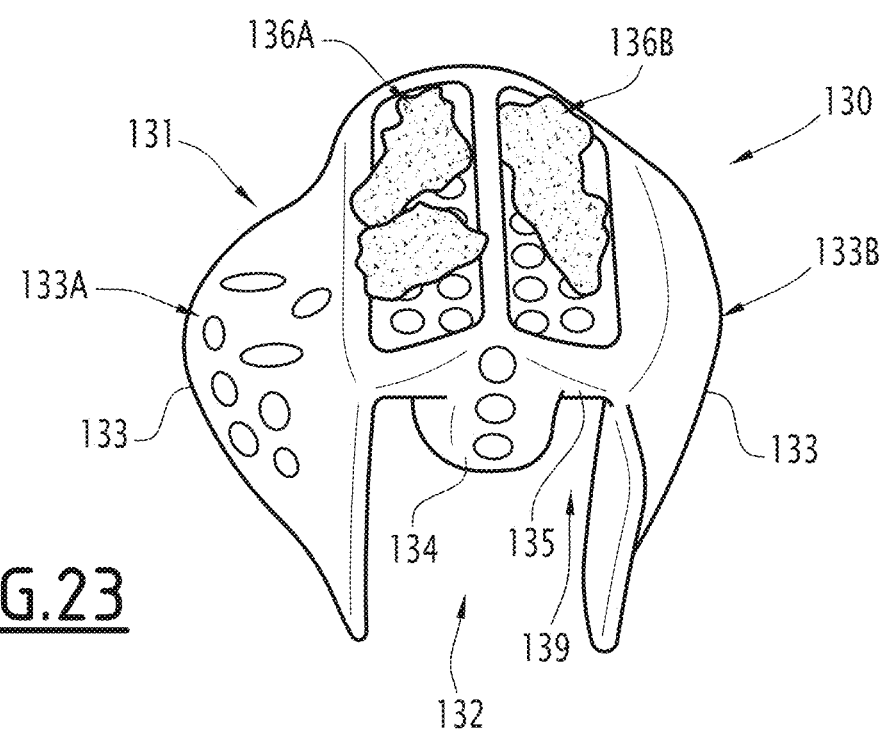

As shown on FIG. 23, instead of an opening 136, two separate openings 136A and 136B may be provided for respectively housing two distinct cores 137 of bone graft in two separate cavities of the exterior part.

The exterior part 131 is preferably configured so that tuberosity fragments reattached to the stem part 1 may bear against the exterior part 131. For this purpose, the peripheral shape of the exterior part is preferably imitating the shape of the epiphyseal part of the fractured bone. In the illustrated example, a respective peripheral surface 133A and 133B of the wings 133 is shaped for bearing of one respective tuberosity fragment. The surface 133A of a first wing 133 is shaped for receiving a greater tuberosity fragment, while the surface 133B of the second wing 133 is shaped for receiving a lesser tuberosity fragment. Thus, as best visible on FIG. 23, the shapes of the surfaces 133A and 133B of the wings 133 may not be symmetrical to each other, depending on the tuberosity fragment to be reattached thereto.

This exterior part 131 is especially adapted for reattaching thin or fragile tuberosity fragments. Once reattached, such fragments are structurally supported by the wings 133.

A single type of stem part 1 may be used for different situations, depending of the shape of the part 131 secured thereto. For example, if a part of symmetrical shape than the part 131 shown on FIGS. 20 to 23 is equipped onto the same stem part 1, the prosthesis may be used for healing a symmetrical fractured long bone of the patient.

The peripheral shell of the part 131 may be of the same material than the one mentioned for the above-disclosed peripheral shells, preferably one of the above-mentioned biomaterials. The peripheral shell may have barbs as mentioned for the above disclosed peripheral shells, said barbs being for example protruding outwardly from the wings and/or from the central body. The peripheral shell is preferably provided with series of macroscopic through-holes or blind holes leading outwards, formed in the wings 133, for promoting bone ingrowth. "Macroscopic" means that the holes may have a size superior to 0.5 mm. Instead, smaller holes or porosities may be provided for a similar effect, depending on the application.

In an embodiment, the implant 130 comprises, additionally to the exterior part 131, one of the internal parts described above for the other embodiments. In this case, the internal part is secured within the gap 9. The exterior part 131 is advantageously secured to the internal part, preferably by means of one or more fasteners, passing through one of the openings 11, 13 or 15.

FIGS. 24 to 26 show an implant 140 comprising an exterior part 141. The exterior part 141 comprises essentially the same features than the part 131 of the implant 130, including preferably two wings 143, a central body 145, an axial through-opening 149, an aperture 142, a rib 144, an internal cavity provided within the central body 145 and an opening 146 leading to it. On FIG. 24, a core 147 of bone graft positioned within the cavity is shown through the opening 146. On FIG. 26, the cavity and the opening 146 are devoid of bone graft core.

The implant 140 differs from the implant 130 in that two additional blind holes, through-holes, or notches 148 are provided through the wings 143. Each of these holes 148 may be used for housing a core 150 of bone graft, as depicted on FIGS. 16 and 17. Preferably, each of the two holes 148 is open on the same side of the part 141 than the opening 146, namely opposite to the aperture 142, as shown on FIGS. 24 and 26. Preferably, each of the two holes 148 is also open within the opening 149, along the internal side of the wings 143, as visible on FIG. 25.

Only one of the holes 148 may be provided. If at least one of the holes 148 is provided, the internal cavity and the opening 146 may be optional, depending on the application.

Also, the respective peripheral surfaces 143A and 143B of the wings 143 are preferably shaped as a cylinder with a circular base, along an axis X143. In the illustrated example, the axis X143 is oriented in an inclined manner relative to axis X1, approximately crossing the center of the spherical shape of the prosthetic head 6, if such head is provided.

Figure 27:
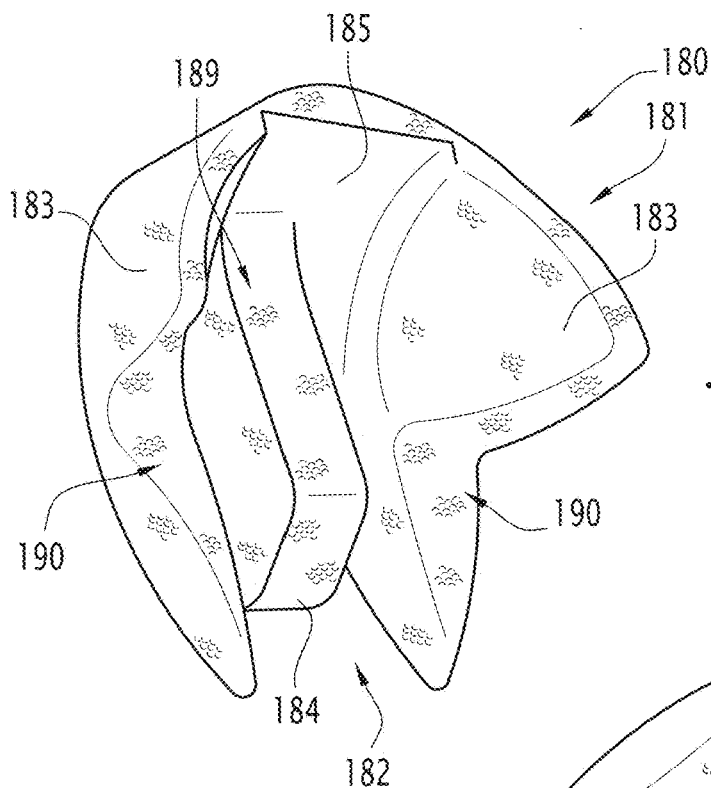
FIGS. 27 and 28 are schematic perspective views of an implant of a prosthesis according to another embodiment of the invention.
Figure 28:
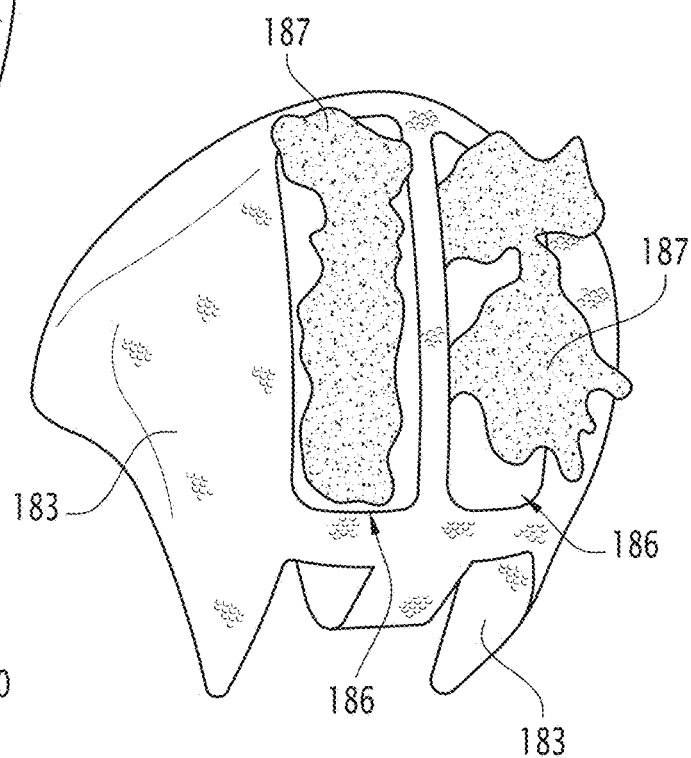

FIGS. 27 and 28 show an implant 180 comprising an exterior part 181. The exterior part 181 is illustrated on FIGS. 27 and 28 respectively with similar perspective orientations than part 131 on FIGS. 22 and 23.

The exterior part 181 comprises essentially the same features than the part 131 of the implant 130, including preferably two wings 183, a central body 185, an axial through-opening 189, an aperture 182, a rib 184, two internal cavities provided within the central body 185 and two respective openings 186 leading to them. On FIG. 28, two cores 187 of bone graft positioned within the cavity are shown through the openings 186.

The implant 180 essentially differs from the implant 130 the surface of the part 181 is devoid of macroscopic holes. Instead, the surface of the part 181 is rough or coarse for promoting bone gripping. Alternatively or additionally to a rough surface, the part 181 may be provided with barbs for a similar effect, depending on the application.

Figure 29:
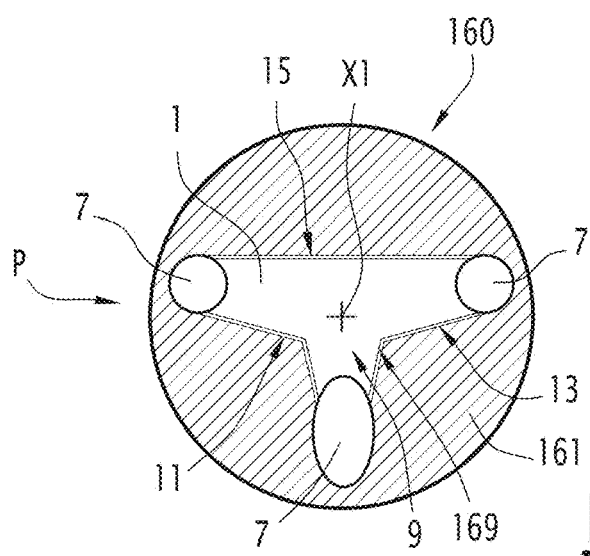
FIG. 29 is a schematic cross-sectional view of a prosthesis according to another embodiment of the invention.

Another difference with the embodiment of FIGS. 20 to 23 is that each wing 183 comprises a respective slot 190. Each slot 190 may be used for housing a bone fragment, cement or bone graft. Each housed element may bear against the epiphyseal end 5 of the stem part 1, radially about axis X1. Each slot 190 opens onto the aperture 182, in a symmetric arrangement relative to each other. As illustrated, each slot 190 is preferably of triangular shape or V-shape. FIG. 29 depicts an embodiment of a prosthesis P including an implant 160 with an exterior part 161 that may have the same features than the part 131 or the part 141, especially relating to the material used, the method for securing the part 161 to the stem part 1, and the fact that a bone graft core may be secured within a cavity thereof. The exterior part 161 may be used in an implant instead of part 131 or 141.

The exterior part 161 wraps the stem part 1 all around axis X1, preferably without aperture like the aperture 132 or 142.

The part 131 comprises an axial through-opening 169, with similar function than the opening 139 or 149. The opening 169 is shaped in correspondence with the contour of the stem part 1, namely is T-shaped. The opening 169 has a closed contour, since no aperture like the aperture 132 or 142 is provided. In this case, when the stem part 1 is inserted into the exterior part 161, said stem part 1 is wrapped by the exterior part 161, forming a sleeve, all around axis X1.

Regardless of the embodiment, all or part of the implant may be obtained by additive manufacturing. In case the implant is made of a single integral part or of a plurality of assembled integral parts, the implant may fully be obtained by additive manufacturing.

What is claimed is:

1. A prosthesis for a fractured long bone, the prosthesis comprising:
    a stem part comprising:
        a rod, configured for being inserted into a medullary cavity of a diaphyseal fragment of the fractured long bone, for securing the stem part to the diaphyseal fragment, and
        an epiphyseal end, fixedly secured to the rod by means of at least one linker leg of the stem part, so that a gap is formed between the epiphyseal end and the rod along said at least one linker leg; and
    an implant distinct from the stem part and comprising:
        an internal part located at least partially within the gap, and
        at least one fastener for fastening epiphyseal fragments of the fractured long bone to the stem part, said at least one fastener being secured to the internal part.

2. The prosthesis according to claim 1, wherein said at least one fastener comprises a screw, positioned into the internal part.

3. The prosthesis according to claim 1, wherein the internal part has an elastic tongue allowing snap-fitting of the internal part into the gap, for securing the internal part to the gap.

4. The prosthesis according to claim 1, wherein the internal part comprises at least one expansible body, having:
    a retracted configuration allowing insertion of the expansible body into the gap, and
    an expanded configuration preventing extraction of the expansible body from the gap, thereby securing the expansible body to the gap, the expansible body being put in the expanded configuration by securing the fastener thereto.

5. The prosthesis according to claim 1, wherein the implant comprises at least one exterior part, at least a partially located at the periphery of the stem part, along said at least one linker leg, said exterior part being secured to the internal part.

6. The prosthesis according to claim 5, wherein:
    the stem part defines a main axis passing through the rod, the gap and the epiphyseal end; and
    said at least one exterior part comprises an axial through-opening, the stem part being inserted through the through-opening along the main axis so as to be at least partially wrapped by the exterior part for securing the exterior part to the stem part.

7. The prosthesis according to claim 1, wherein the internal part comprises a synthetic plastic material.

8. The prosthesis according to claim 7, wherein the synthetic plastic material of the internal part comprises Polyethylene or Poly-Ether-Ether-Ketone.

9. The prosthesis according to claim 1, wherein the internal part comprises a mesh metallic material or a porous metallic material.

10. The prosthesis according to claim 9, wherein the metallic material of the internal part comprises Titanium and/or Nitinol.

11. The prosthesis according to claim 1, wherein at least a part of the implant, comprises a peripheral shell and at least one bone graft core received within the peripheral shell.

12. The prosthesis according to claim 11, wherein said at least a part of the implant, which comprises the peripheral shell and said at least one bone graft core, is the internal part.

13. The prosthesis according to claim 11, wherein the peripheral shell comprises a biomaterial.

14. The prosthesis according to claim 11, wherein the peripheral shell comprises a degradable polymer or degradable metal.

15. The prosthesis according to claim 11, wherein the peripheral shell comprises at least one of the following composites of materials: a composite of hydroxyapatite and tricalciumphosphate, a composite of polylactide-co-glycolide and tricalciumphosphate, a composite of poly-L-lactide and tricalciumphosphate.

16. The prosthesis according to claim 1, wherein the implant comprises barbs protruding outwardly from the implant, outside of the gap.

17. The prosthesis according to claim 1, wherein at least a part of the implant is obtained by additive manufacturing.

18. The prosthesis according to claim 1, wherein the prosthesis is a shoulder prosthesis for a fractured humerus.

* * * * *